(12) United States Patent
Parlikar et al.

(10) Patent No.: US 8,235,910 B2
(45) Date of Patent: Aug. 7, 2012

(54) SYSTEMS AND METHODS FOR MODEL-BASED ESTIMATION OF CARDIAC EJECTION FRACTION, CARDIAC CONTRACTILITY, AND VENTRICULAR END-DIASTOLIC VOLUME

(76) Inventors: Tushar A. Parlikar, Cambridge, MA (US); George C. Verghese, Newton, MA (US); Thomas Heldt, Cambridge, MA (US); Ramakrisna Mukkamala, Lansing, MI (US)

( * ) Notice: Subject to any disclaimer, the term of this patent is extended or adjusted under 35 U.S.C. 154(b) by 1054 days.

(21) Appl. No.: 12/121,878

(22) Filed: May 16, 2008

(65) Prior Publication Data

US 2008/0294057 A1 Nov. 27, 2008

Related U.S. Application Data

(60) Provisional application No. 60/938,257, filed on May 16, 2007.

(51) Int. Cl.
*A61B 5/02* (2006.01)
(52) U.S. Cl. ..................................................... 600/485
(58) Field of Classification Search .................. None
See application file for complete search history.

(56) References Cited

U.S. PATENT DOCUMENTS

| | | | |
|---|---|---|---|
| 4,236,527 A | 12/1980 | Newbower et al. | |
| 4,507,974 A | 4/1985 | Yelderman | |
| 5,146,414 A | 9/1992 | McKown et al. | |
| 5,153,178 A | 10/1992 | Maroko | |
| 5,400,793 A | 3/1995 | Wesseling | |
| 5,687,733 A | 11/1997 | McKown | |
| 6,485,431 B1 | 11/2002 | Campbell | |
| 6,758,822 B2 | 7/2004 | Romano | |
| 2003/0040675 A1 | 2/2003 | Sharrock | |
| 2004/0158163 A1 | 8/2004 | Cohen et al. | |
| 2004/0249297 A1 | 12/2004 | Pfeiffer et al. | |
| 2004/0254483 A1* | 12/2004 | Zdeblick et al. | 600/486 |
| 2005/0015009 A1 | 1/2005 | Mourad et al. | |
| 2005/0096557 A1 | 5/2005 | Vosburgh et al. | |
| 2005/0124903 A1 | 6/2005 | Roteliuk et al. | |
| 2005/0124904 A1 | 6/2005 | Roteliuk | |
| 2006/0008923 A1 | 1/2006 | Anderson et al. | |
| 2006/0178589 A1 | 8/2006 | Dobak | |
| 2006/0235323 A1 | 10/2006 | Hatib et al. | |
| 2007/0016031 A1 | 1/2007 | Mourad et al. | |
| 2007/0024946 A1 | 2/2007 | Panasyuk et al. | |
| 2007/0197921 A1* | 8/2007 | Cohen et al. | 600/485 |
| 2008/0015451 A1 | 1/2008 | Hatib et al. | |
| 2008/0287753 A1 | 11/2008 | Parlikar et al. | |
| 2008/0287812 A1 | 11/2008 | Parlikar et al. | |
| 2009/0112113 A1 | 4/2009 | Mukkamala et al. | |

FOREIGN PATENT DOCUMENTS

| | | |
|---|---|---|
| WO | WO-2007/109059 A2 | 9/2007 |
| WO | WO-2008/144404 A1 | 11/2008 |
| WO | WO-2008/144525 A1 | 11/2008 |

OTHER PUBLICATIONS

International Preliminary Report on Patentability and Written Opinion for International Application No. PCT/US2008/063872 dated Nov. 26, 2009.
Cheatham et al., "Shock: An Overview," Orlando Regional Medical Center, 2004, available online at http://www.surgicalcriticalcare.net/Lectures/shock_overview.pdf.
Parlikar et al., "Cycle-Averaged Models of Cardiovascular Dynamics" IEEE Trans. on Circuits and Systems—1, vol. 53, No. 11, pp. 2459-2468, Nov. 2006.
International Search Report of the International Searching Authority for International Application No. PCT/US08/63872 dated Sep. 22, 2008.
Written Opinion of the International Searching Authority for International Application No. PCT/US08/63872 dated Sep. 22, 2008.
International Preliminary Report on Patentability and Written Opinion for International Application No. PCT/US2008/063725 dated Nov. 26, 2009.
International Preliminary Report on Patentability and Written Opinion for International Application No. PCT/US2008/063915 dated Nov. 26, 2009.
International Search Report and Written Opinion of the International Searching Authority for International Application No. PCT/US08/63725 dated Sep. 26, 2008.
International Search Report and Written Opinion of the International Searching Authority for International Application No. PCT/US08/63915 dated Oct. 3, 2008.
Parlikar et. al., "Model-based estimation of cardiac output and total peripheral resistance," Computer in Cardiology, vol. 34 (2007), pp. 379-382.

* cited by examiner

*Primary Examiner* — Tracy Vivlemore
(74) *Attorney, Agent, or Firm* — Ropes & Gray LLP

(57) ABSTRACT

The methods and systems for estimating cardiac ejection fraction, cardiac contractility, and ventricular end-diastolic volume on a beat-by-beat basis include observing arterial blood pressure waveforms to determine ventricular compliances for a pressure-volume loop in the ventricle. Uncalibrated or calibrated cardiac ejection fraction may be calculated from estimates of stroke volume and the ventricular compliances. Cardiac contractility may be calculated from estimates of a ventricular compliance. Uncalibrated or calibrated ventricular end-diastolic volume may also be calculated from estimates of stroke volume and the ventricular compliances. A set of calibration parameters for calibrating cardiac ejection fraction or ventricular end-diastolic volume may be estimated in a least-squares manner.

58 Claims, 9 Drawing Sheets

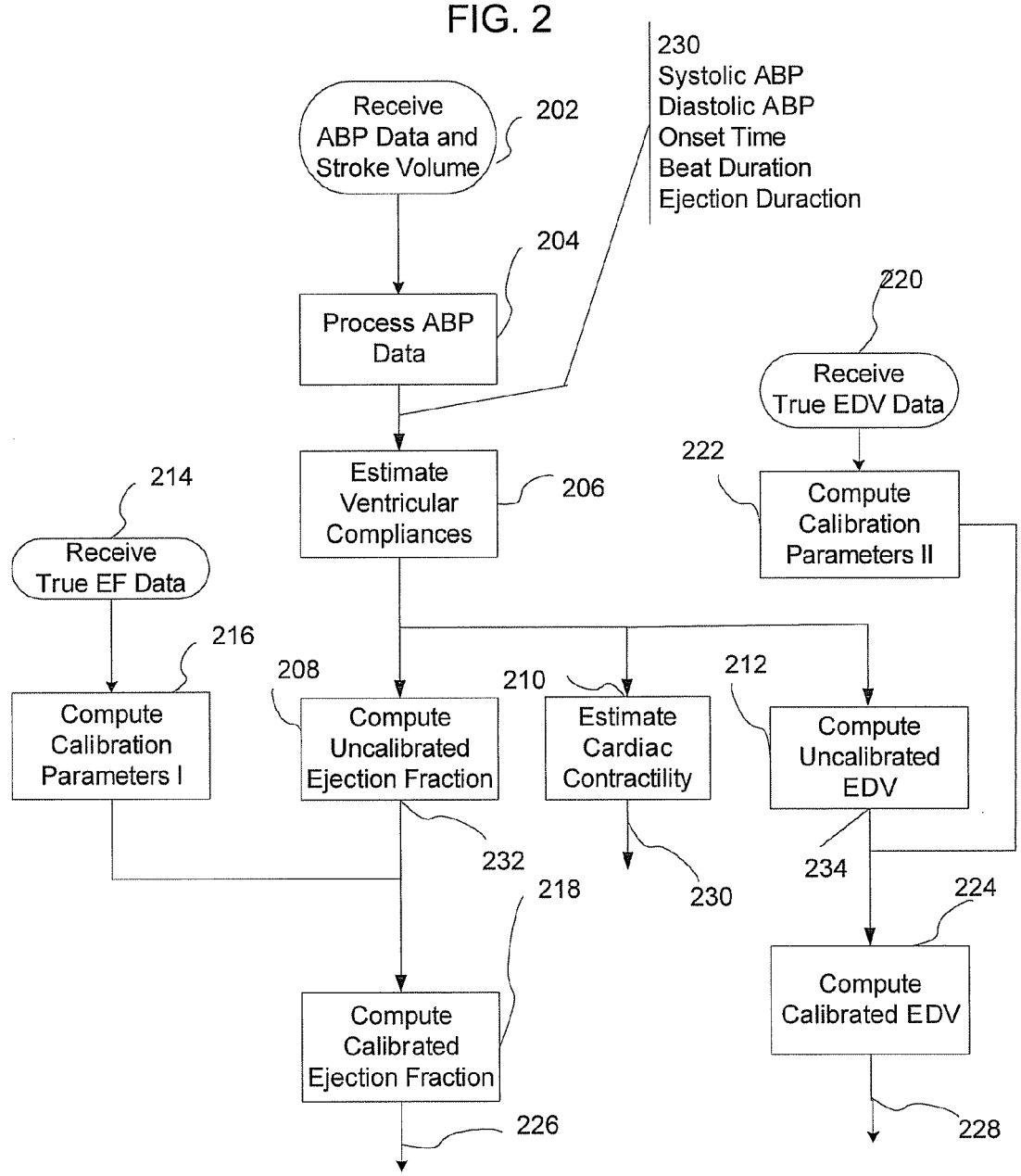

FIG. 6

| Dog | EF (%) Range | LVEDV (ml) Range | LVESV (ml) Range | HR (bpm) Range | cABP (mmHg) Range |
|---|---|---|---|---|---|
| 1 | 53-90 | 28-46 | 3-20 | 94-181 | 50-160 |
| 2 | 30-86 | 17-30 | 3-21 | 88-179 | 56-99 |
| 3 | 55-76 | 19-28 | 6-11 | 142-197 | 57-120 |

FIG. 7

| Dog | Number of comparisons | RMSNE (%) using cABP | RMSNE (%) using fABP | RMSNE (%) using carABP |
|---|---|---|---|---|
| 1 | 7 | 14.1 | 11.6 | 16.1 |
| 2 | 29 | 11.7 | – | – |
| 3 | 7 | 13.6 | – | – |
| Aggregate | 43 | 12.6 | – | – |

FIG. 8

| Dog | Number of comparisons | RMSNE (%) for SH EF | RMSNE (%) using cABP | RMSNE (%) using fABP | RMSNE (%) using carABP |
|---|---|---|---|---|---|
| 1 | 7 | 20.3 | 14.0 | 11.5 | 16.0 |
| 2 | 29 | 13.7 | 12.1 | – | – |
| 3 | 7 | 6.8 | 13.2 | – | – |
| Aggregate | 43 | 13.9 | 12.7 | – | – |

FIG. 9

| Dog | Number of comparisons | RMSNE (%) for SH LVEDV | RMSNE (%) using cABP | RMSNE (%) using fABP | RMSNE (%) using carABP |
|---|---|---|---|---|---|
| 1 | 7 | 17.5 | 14.3 | 15.5 | 15.4 |
| 2 | 29 | 14.0 | 9.8 | – | – |
| 3 | 7 | 6.1 | 14.0 | – | – |
| Aggregate | 43 | 13.3 | 11.9 | – | – |

SYSTEMS AND METHODS FOR MODEL-BASED ESTIMATION OF CARDIAC EJECTION FRACTION, CARDIAC CONTRACTILITY, AND VENTRICULAR END-DIASTOLIC VOLUME

CROSS REFERENCE TO RELATED APPLICATIONS

The instant application claims priority from provisional application No. 60/938,257 filed May 16, 2007, the disclosure of which is incorporated herein by reference in its entirety.

STATEMENT REGARDING FEDERALLY SPONSORED RESEARCH OR DEVELOPMENT

This invention was made with Government support under Contract No. R01 EB001659, awarded by the National Institute of Biomedical Imaging and Bioengineering, a part of the United States' National Institutes of Health, and Contract No. CA00403 awarded by the National Space Biomedical Research Institute. The Government has certain rights in this invention.

FIELD OF THE INVENTION

This invention relates to cardiac ejection fraction, cardiac contractility, and ventricular end-diastolic volume estimation and more particularly to cardiac ejection fraction, cardiac contractility, and ventricular end-diastolic volume estimation from peripheral or central arterial blood pressure waveforms.

BACKGROUND OF THE INVENTION

Several cardiovascular variables are used clinically to assess the performance of the heart as an effective pump. Chief among them are the end-diastolic volume and pressure, contractility, and ejection fraction (all defined below), usually—but not limited to—those pertaining to the left ventricle.

End-diastolic volume (EDV) is the volume in the ventricle at the end of the ventricular filling period of the cardiac cycle. End-systolic volume (ESV) is the volume in the ventricle at the end of the ejection period of the cardiac cycle.

Stroke volume (SV) of the heart or of the left or right ventricle may be defined as the difference between corresponding end-systolic and end-diastolic volumes, namely:

$$SV = EDV - ESV \quad (EQ. 1)$$

Cardiac output (CO) is the amount of blood the heart pumps out over a unit of time. Typical values of CO in resting adults range from 3 liters/minute to 6 liters/minute. One basis for estimating or measuring CO is the formula $CO = HR \times SV$, where SV is cardiac stroke volume and HR is heart rate. If SV is measured in liters/beat and HR is measured in beats/minute, then CO is given in liters/minute, although any other units of volume and time may be used. Another basis for estimating or measuring CO is the formula $CO = MAP/TPR$, where MAP is mean arterial blood pressure and TPR is total peripheral resistance.

Ejection fraction (EF) is defined as the ratio of the stroke volume (SV) to the ventricular end-diastolic volume (EDV) and is expressed in percent, namely:

$$EF = SV/EDV = (EDV - ESV)/EDV \quad (EQ. 2)$$

More simply, EF represents the percentage of the end-diastolic volume of a ventricular chamber that is ejected per beat. EF can be measured in the right ventricle (RV) or the left ventricle (LV). Thus, RVEF is right ventricular ejection fraction and LVEF is left ventricular ejection fraction.

In this application, embodiments are presented with respect to the left ventricle, for which Applicants sometimes write EF instead of LVEF. The methods and systems described herein can easily be extended to the right ventricle.

Cardiac contractility is a measure of ventricular elastance at the end of the ejection.

Chronically elevated end-diastolic pressures and volumes indicate poor pump performance, as do low states of contractility and a reduced ejection fraction [1]. (Numbers in square brackets refer to the reference list included herein. The contents of all these references are incorporated herein by reference.) Ideally, these variables should be measured non- to minimally invasively for establishing initial diagnoses and tracked continuously for monitoring of disease progression and titration of therapeutic interventions. The current clinical gold-standard measurements for measuring these variables, however, are costly, require expert operators, and are only performed intermittently Cardiac volumes are commonly measured echocardiographically: a skilled operator performs intermittent ultrasonic evaluations of the heart during which the relevant cardiac volumes are determined. Cardiac ejection fraction is then calculated from the resultant end-systolic and end-diastolic volume estimates.

The pulmonary capillary wedge pressure is used as a surrogate for the left ventricular end-diastolic pressure (the 'preload' of the left ventricle). The 'wedge pressure' measurement is highly invasive, requiring a Swan-Ganz catheter to be advanced through the right atrium and right ventricle and placed into a main branch of the pulmonary artery. When a balloon at the catheter's tip is inflated to block flow temporarily, the pressure distal to the balloon equilibrates with the pressure at the level of the pulmonary vein. The resultant pressure is taken to be left-ventricular end-diastolic pressure. Some Swan-Ganz catheters are specially equipped with rapid-response thermistors that allow for estimation of right ventricular volumes and therefore right ventricular ejection fraction [2]. Due to its highly invasive nature, the Swan-Ganz catheter is rarely used outside the intensive care or the perioperative care environments and even in these settings, its benefits are increasingly being questioned [5, 6].

Contractility is an important concept in cardiac physiology and clinical cardiology. Changes in cardiac contractility pertain to the heart's ability to change its systolic contractile state so as to adjust its effectiveness as a pump. Cardiac contractility, however, is never directly assessed clinically, as a direct measurement would entail acquiring ventricular volume and pressure simultaneously while rapidly varying the loading (filling) conditions of the heart. (Rapid changes in loading conditions are required such that contractility is not changed by cardiovascular reflex mechanisms during the course of the measurement.) Such a procedure requires one ventricular catheter to measure pressure, possibly a balloon catheter in the vena cava to vary the heart's loading conditions, and an accurate method to measure ventricular volume rapidly. A clinical measure of cardiac contractility is the maximum rate of change of ventricular pressure during the isovolumic contraction phase of the cardiac cycle. In the clinically more important left ventricle, such an assessment of contractility would require left-sided cardiac catheterization. This is never done routinely except possibly in patients undergoing cardiac catheterization for symptoms of shortness-of-breath or assessment of valve dysfunction.

As reported in WIPO patent application publication No. WO2007109059 to Mukkamala, the contents of which are incorporated herein in their entirety, to improve upon the significant disadvantages shared by imaging techniques, a few methods have been introduced for continuous and automatic monitoring of EF or ventricular volume. These methods include continuous thermodilution technique, the non-imaging nuclear monitor, the conductance catheter, and sonomicrometry. However, these methods are all limited in at least one clinically significant way.

The continuous thermodilution method involves automatic heating of blood in the right ventricle via a thermal filament, measurement of the temperature changes downstream in the pulmonary artery via a fast response thermistor, construction of a bolus thermodilution washout decay curve, and estimation of RVEF based on the extent of the temperature decay over a cardiac cycle. An attractive feature of this method is that it requires only a pulmonary artery catheterization, which is occasionally performed in a subset of critically ill patients (see below). As a result, the method is sometimes conducted in clinical practice, though it has not gained widespread popularity. On the other hand, the method does not provide beat-to-beat estimates of RVEF but rather estimates at time intervals of approximately a minute or more. Furthermore, the method continually perturbs the circulation and is not amenable to ambulatory or home health care monitoring, both of which could potentially reduce hospital admissions and health care costs. Perhaps the most significant limitation of this method is that it cannot be utilized to determine the more clinically relevant LVEF.

In contrast, the non-imaging nuclear monitor, the conductance catheter, and sonomicrometry do permit automatic, beat-by-beat monitoring of LVEF. However, as discussed below, the substantial limitations of each of these methods have precluded their use in clinical practice.

In non-imaging nuclear monitoring of LVEF, the patient is given an injection of a radioactive tracer, which distributes throughout the circulation. The amount of the radioactive tracer in the LV is then measured with a crystal scintillation detector attached to a single bore converging collimator. The method is able to monitor LV volume at a high temporal resolution (10 ms) by sacrificing the spatial resolution, which would otherwise be needed to produce images. An appealing feature of the method is that LVEF is estimated without any assumptions about ventricular geometry. Additionally, systems have been developed for both bedside and ambulatory monitoring. However, the method is not in clinical use because of the difficulty in positioning the detector at the appropriate location on the patient's chest and in correcting for background radioactivity originating from extra-cardiac regions. The method also has the obvious disadvantage of exposing the patient to radiation.

The conductance catheter method involves placing a multi-electrode catheter in a ventricular cavity, continually applying AC current to the electrodes to generate an electric field, measuring the resulting voltage gradients, and estimating the ventricular volume from the intra-ventricular conductance using geometric assumptions. Thus, the method is able to provide estimates of either LVEF or RVEF. However, for LVEF, the method requires a left heart catheterization, which is rarely performed in critically-ill patients. Moreover, the method is not capable of accurately estimating absolute or proportional ventricular volume, which is needed to reliably compute EF, due mainly to the parallel conductance (offset error) and non-uniformity of the generated electric field (scale factor error). Finally, another disadvantage of this method is that it is not amenable to ambulatory or home health care monitoring.

Sonomicrometry involves suturing crystals to opposite sides of the ventricular endocardium and using the ultrasound transit time principle to estimate the ventricular volume based on geometric assumptions. While the method can provide accurate estimates of either LVEF or RVEF when a sufficient number of crystals are used, it is obviously much too invasive to ever be employed in clinical practice.

It would be desirable to be able to accurately monitor beat-by-beat LVEF and/or beat-by-beat RVEF based on the mathematical analysis of continuous blood pressure. It would be desirable to be able to accurately monitor beat-by-beat EDV and/or beat-by-beat cardiac contractility based on the mathematical analysis of continuous blood pressure. Continuous blood pressure is routinely monitored in clinical practice and several systems are currently available for continuous monitoring of specifically systemic arterial blood pressure (SABP, e.g., invasive catheters, non-invasive finger-cuff photoplethysmography, non-invasive arterial tonometry, and implanted devices), LV pressure (LVP, e.g., implanted devices), pulmonary artery pressure (PAP, e.g., invasive pulmonary artery catheters and implanted devices), and RVP (e.g., invasive pulmonary artery catheters and implanted devices). Thus, in contrast to the aforementioned methods, this approach would readily permit continuous and automatic measurement of LVEF and RVEF in the context of several important clinical applications. For example, such an approach could be applied to: (1) routinely employed invasive SABP and PAP catheter systems for titrating therapy in the intensive care unit (ICU), continuous monitoring of cardiac surgery in the operating room (OR), and remote ICU monitoring; (2) implanted SABP, PAP, RVP, and LVP systems for chronic, ambulatory monitoring of cardiovascular disease and facilitating the diagnosis of ischemia with surface ECGs; and 3) non-invasive SABP systems for emergency room (ER) or home health care monitoring. Note that these clinical applications of continuous and automatic EF monitoring have, for the most part, not been realized with the currently available measurement methods. Moreover, a blood pressure-based approach could estimate EF without making any assumptions about the ventricular geometry.

In WIPO patent application publication No. WO2007109059 to Mukkamala, systems and methods for estimating EF from a central arterial blood pressure waveform are described. These systems and methods assume a particular ventricular elastance function and performing an intra-beat fit of this function to the central arterial blood pressure (cABP) waveform. The method of Mukkamala is thus still quite invasive. However, it does not require calibration against true or reference EF measurements.

Thus, methods and apparatus for effectively monitoring beat-by-beat EF, beat-by-beat EDV, and beat-by-beat contractility, are extremely desirable in that they would greatly facilitate the monitoring, diagnosis, and treatment of cardiovascular disease. In addition, if these methods and apparatus could be noninvasive or minimally-invasive, such that only a peripheral blood pressure waveform is required, they would be quite useful.

The statements in this section merely provide background information related to the present disclosure and may not constitute prior art

SUMMARY OF THE INVENTION

One of the objects of the present invention is to provide systems and methods for continuous beat-by-beat monitoring of cardiac end-diastolic volume, contractility, and ejection fraction through processing of an arterial blood pressure waveform. The embodiments described below will use, for illustrative purposes only, a systemic arterial blood pressure signal and the left ventricle. However, those skilled in the art will recognize that these examples would translate directly to the monitoring of right-ventricular performance by analyzing the pulmonary artery pressure waveform.

Instead of fitting an intra-beat central ABP waveform, Applicants propose a ventricular pressure-volume model-based method that uses inter-beat information from the arterial blood pressure waveform—central or peripheral—to estimate EF, cardiac contractility, and EDV. Such a method does not require one to assume a particular ventricular elastance function; it exploits the inter-beat variability in systolic and diastolic arterial blood pressures to estimate important ventricular parameters.

In one aspect, the invention relates to a method for estimating beat-by-beat cardiovascular parameters and variables, comprising processing one or more cycles of arterial blood pressure to determine intra-beat and inter-beat variability in blood pressure, and computing estimates of one or more cardiovascular parameters and variables from the intra-beat variability, the inter-beat variability, beat-by-beat estimates of stroke volume, and a ventricular pressure-volume model.

In some embodiments, the arterial blood pressure is measured at a central artery of the cardiovascular system. In an embodiment, the central artery is the aorta. In another embodiment, the arterial blood pressure is measured at a peripheral artery of the cardiovascular system. In an embodiment, the arterial blood pressure is measured at a pulmonary artery of the cardiovascular system. In some embodiments, the arterial blood pressure is measured using a noninvasive blood pressure device. In one embodiment, the noninvasive blood pressure device may be a photoplethysmographic blood pressure device. In another embodiment, the noninvasive blood pressure device may be a tonometric blood pressure device.

In some embodiments, processing the one or more cycles of arterial blood pressure includes obtaining a diastolic blood pressure, a peak-systolic blood pressure, and an end-systolic blood pressure for each cycle. In another embodiment, processing the one or more cycles of arterial blood pressure includes obtaining an onset time for each cycle or obtaining a beat duration for each cycle. In an embodiment, the end-systolic blood pressure is estimated using an estimate of the duration of ventricular ejection. Optionally, the estimate of the duration of ventricular ejection may be obtained using phonocardiographic measurements.

In one embodiment, actual measurements of the stroke volume are used instead of stroke volume estimates. In another embodiment, information from phonocardiographic measurements are used. The phonocardiographic information may include parameters relating to the beat-by-beat timing of cardiac cycle events. The parameters relating to the beat-by-beat timing of cardiac cycle events may include the duration of ventricular ejection.

In another embodiment, the cardiovascular parameters and variables include at least one of a beat-by-beat pre-ejection ventricular compliance, a beat-by-beat end-diastolic compliance, a beat-by-beat end-systolic ventricular compliance, and a beat-by-beat peak-systolic compliance. In one embodiment, at least one of the beat-by-beat pre-ejection ventricular compliance, the beat-by-beat end-systolic ventricular compliance, the beat-by-beat end-diastolic compliance, and the beat-by-beat peak-systolic compliance is for the left ventricle. In another embodiment, at least one of the beat-by-beat pre-ejection ventricular compliance, the beat-by-beat end-systolic ventricular compliance, the beat-by-beat end-diastolic compliance, and the beat-by-beat peak-systolic compliance is for the right ventricle.

In a further embodiment, at least one of the beat-by-beat pre-ejection ventricular compliance, the beat-by-beat end-systolic ventricular compliance, and the beat-by-beat peak-systolic compliance is estimated over a data window. Optionally, at least one of the beat-by-beat pre-ejection ventricular compliance, the beat-by-beat end-systolic ventricular compliance, and the beat-by-beat peak-systolic compliance is estimated through optimization of an error criterion. In some embodiments, the error criterion is a least-squared error.

In an embodiment, the cardiovascular parameters and variables include an uncalibrated beat-beat ejection fraction. In a further embodiment, the method includes the step of computing calibrated beat-by-beat ejection fraction from the uncalibrated beat-by-beat ejection fraction using one or more calibration parameters. In an embodiment, the calibration parameters may be computed using an optimization criterion. Optionally, the calibration parameters may be computed for each of the beats. In some embodiments, the calibration parameters may include ventricular dead volume and/or intra-thoracic pressure.

In another embodiment, the cardiovascular parameters and variables include uncalibrated beat-by-beat end-diastolic volume. In a further embodiment, the method includes the step of computing calibrated beat-by-beat end-diastolic volume from the uncalibrated beat-by-beat end-diastolic volume using a second set of calibration parameters. In an embodiment, the calibration parameters may be computed using an optimization criterion. Optionally, the calibration parameters may be computed for each of the beats. In some embodiments, the calibration parameters may include ventricular dead volume and/or intra-thoracic pressure.

In a further embodiment, the method includes computing beat-by-beat cardiac contractility.

According to another aspect, the invention relates to a system for estimating beat-to-beat cardiac output comprising a blood pressure measuring device, a processor, a display, a user interface, and a memory-storing computer executable instructions, which when executed by the processor cause the processor to receive one or more cycles of arterial blood pressure from the blood pressure device, receive beat-to-beat estimates of stroke volume, analyze one or more cycles of arterial blood pressure to determine intra-beat and inter-beat variability in blood pressure, compute estimates of one or more cardiovascular parameters and variables from the intra-beat variability, the inter-beat variability, beat-to-beat estimates of stroke volume, and a ventricular pressure-volume model, and display the estimates.

BRIEF DESCRIPTION OF THE DRAWINGS

The invention may be better understood from the following illustrative description with reference to the following drawings.

FIG. 2 is a process flow diagram suitable for estimating cardiac ejection fraction, cardiac contractility, and ventricular end-diastolic volume with the system of FIG. 1, according to an illustrative embodiment of the invention;

FIG. 6 is a table of population statistics for the canine animal experiment data set. The data was obtained from Professor Ramakrishna Mukkamala at Michigan State University and was also used in [3];

FIG. 7 is a table of RMSNEs for Applicants' mean-calibrated EF estimate using cABP, fABP, or carABP, with window size=50 beats (using 2 points in each window) and $Q^d=5$ ml;

FIG. 8 is a table of RMSNEs for Applicants' single point-calibrated EF estimate using cABP, fABP, or carABP, with window size=50 beats (using 2 points in each window) and $Q_d=5$ ml;

FIG. 9 is a table of RMSNEs for Applicants' mean-calibrated LVEDV estimate, for which EF was calculated with window size=50 beats and $Q_d=5$ ml;

DESCRIPTION OF CERTAIN ILLUSTRATIVE EMBODIMENTS

To provide an overall understanding of the invention, certain illustrative embodiments will now be described. However, it will be understood by one of ordinary skill in the art that the methods described herein may be adapted and modified as is appropriate for the application being addressed and that the systems and methods described herein may be employed in other suitable applications, and that such other additions and modifications will not depart from the scope hereof.

Figure 1:
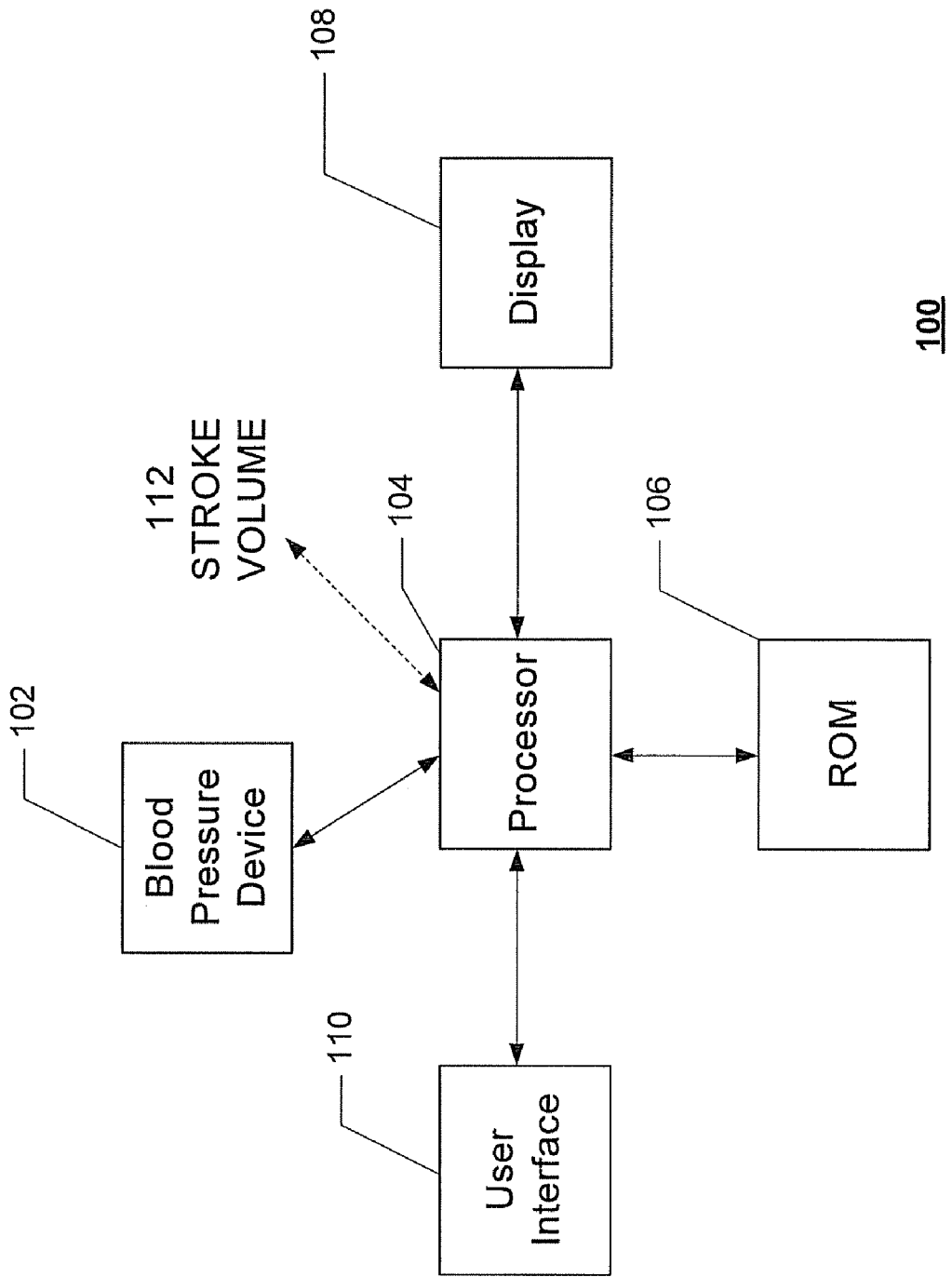
FIG. 1 is a block diagram of a system for estimating cardiac ejection fraction, cardiac contractility, and ventricular end-diastolic volume, according to an illustrative embodiment of the invention.

FIG. 1 is a block diagram of an estimation system 100 in which the present invention's teachings may be implemented. The estimation system 100 includes blood pressure measuring device 102, stroke volume data 112, processor 104, memory 106 e.g. Read-Only Memory (ROM), display 108, and user interface 110. The processor 104 operates on blood pressure data from blood pressure measuring device 102 and stroke volume data 112 in accordance with computer executable instructions loaded into memory 106. The instructions will ordinarily have been loaded into the memory from local persistent storage in the form of, say, a disc drive with which the memory communicates. The instructions may additionally or instead be received by way of user interface 110. The system may also receive user input from devices such as a keyboard, mouse, or touch-screen. Blood pressure measuring device 102 may be an invasive or a noninvasive device. Blood pressure measuring device 102 may be a photoplethysmographic device, a tonometric device, or a catheter-based system. The blood pressure may be measured at a central, a pulmonary, or a peripheral artery in the cardiovascular system.

The stroke volume estimates 112 operated on by processor 104 of estimation system 100 of FIG. 1 may be obtained, for instance, using methods described in [3] or [4], or other CO or SV estimation systems. Examples include systems directed to estimating CO (and hence SV) via thermodilution e.g. U.S. Pat. No. 4,236,527 to Newbower et al., U.S. Pat. No. 4,507,974 to Yelderman, U.S. Pat. No. 5,146,414 to McKown et al., and U.S. Pat. No. 5,687,733 to McKown et al., the contents of each of which are incorporated herein in their entirety, or systems directed to estimating CO (and hence SV) from arterial blood pressure measurements, e.g., U.S. Pat. No. 5,400,793 to Wesseling, U.S. Patent Application Publication No. 20040158163 to Cohen et al., U.S. Patent Application Publication No. 20050124903 to Roteliuk et al., U.S. Patent Application Publication No. 20050124904 to Roteliuk, U.S. Patent Application Publication No. 20060235323 to Hatib et al., U.S. Patent Application Publication No. 20080015451 to Hatib et al., the contents of each of which are incorporated herein in their entirety.

FIG. 2 is a process flow diagram 200 including steps 202, 204, 206, 208, 210, 212, 214, 216, 218, 220, 222, 224 suitable for estimating ejection fraction, cardiac contractility, and end-diastolic volume with estimation system 100 of FIG. 1, according to an illustrative embodiment of the invention. Blood pressure measuring device 102 measures arterial blood pressure waveforms and transmits the ABP waveform data to processor 204 of cardiac output estimation system 100 of FIG. 1 in step 202. In step 202, stroke volume estimates 112 (either estimated SV or actual reference SV measurements) are also received by processor 104 of estimation system 100 of FIG. 1.

In step 204 of process 200 in FIG. 2, processor 104 of estimation system 100 of FIG. 1 receives one or more cycles of ABP data and processes the ABP data. As will be explained in detail with reference to FIGS. 3-12, the outputs 212 of step 204 may include diastolic arterial blood pressure, systolic arterial blood pressure, cycle onset time, and cycle length, for each of the received cycles of the arterial blood pressure. Note that in this application, beat and cycle are used interchangeably. Thus, cardiac cycle and cardiac beat are equivalent terms.

In step 206 of process 200 in FIG. 2, as will be explained below in reference to FIGS. 3-12, processor 104 of estimation system 100 estimates one or more ventricular compliances for a ventricular pressure-volume model. These compliances may include at least one of a beat-by-beat pre-ejection ventricular compliance, a beat-by-beat end-diastolic compliance, a beat-by-beat end-systolic ventricular compliance, and a beat-by-beat peak-systolic compliance. These ventricular compliances are used in steps 208, 210, and 212 of process 200 in FIG. 2, to obtain estimates of uncalibrated beat-by-beat ejection fraction 232, cardiac contractility 230, and beat-by-beat uncalibrated end-diastolic volume 234, respectively. Calibrated ejection fraction 226 can be obtained using one or more reference or true ejection fraction measurements in steps 214, 216, and 218. Additionally, calibrated end-diastolic volume 228 may be obtained using one or more reference or true end-diastolic volume measurements in steps 220, 222, and 224.

In this manner, beat-by-beat ejection fraction, beat-by-beat cardiac contractility, and beat-by-beat end-diastolic volume may be estimated robustly because estimation system 100 of FIG. 1 uses intra- and inter-beat variability in the arterial blood pressure waveforms, instead of the actual waveforms themselves. As will be described below in reference to FIGS. 3-12, the results obtained, using estimation system 100 of FIG. 1, are accurate enough for clinical application.

In the discussion below, Applicants will describe some embodiments in more detail. Applicants will begin with a description of a ventricular pressure-volume model with reference to FIGS. 3-4. Although only the left ventricular pressure-volume model is presented here, the derivations and results directly translate to right ventricular pressure-volume models. This description will be followed by a derivation of the methods for estimating beat-by-beat ejection fraction, beat-by-beat contractility, and beat-by-beat end-diastolic volume, with reference to FIGS. 3-5. Linear least-squares estimation error criterion method for the parameters and variables of the ventricular pressure-volume model will also be presented. Calibration parameters, and methods for estimating these parameters, including a linear least-squares estimation error criterion method, will also be presented. Applicants conclude this section with a detailed description of experimental results using an animal (canine or dog) data set, with reference to FIGS. 6-12.

Ventricular Pressure-Volume Models

End-diastolic volume, EDV, is given by the sum of the end-diastolic unstressed volume, $V_{ed}^O$, and the end-diastolic stressed volume, $V_{ed}^S$:

$$EDV \equiv V_{ed}^O + V_{ed}^S \qquad (\text{EQ. 3})$$

Figure 3A:
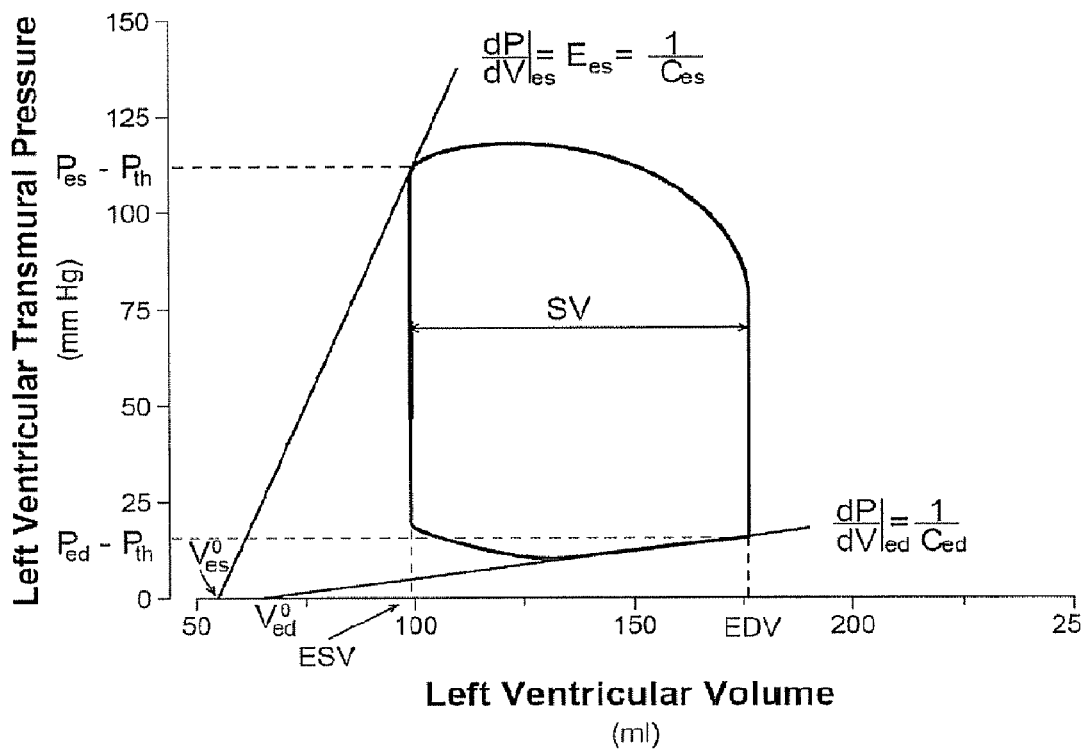
FIG. 3a shows a left ventricular pressure-volume loop with important cardiovascular parameters and variables labeled.
Figure 3B:
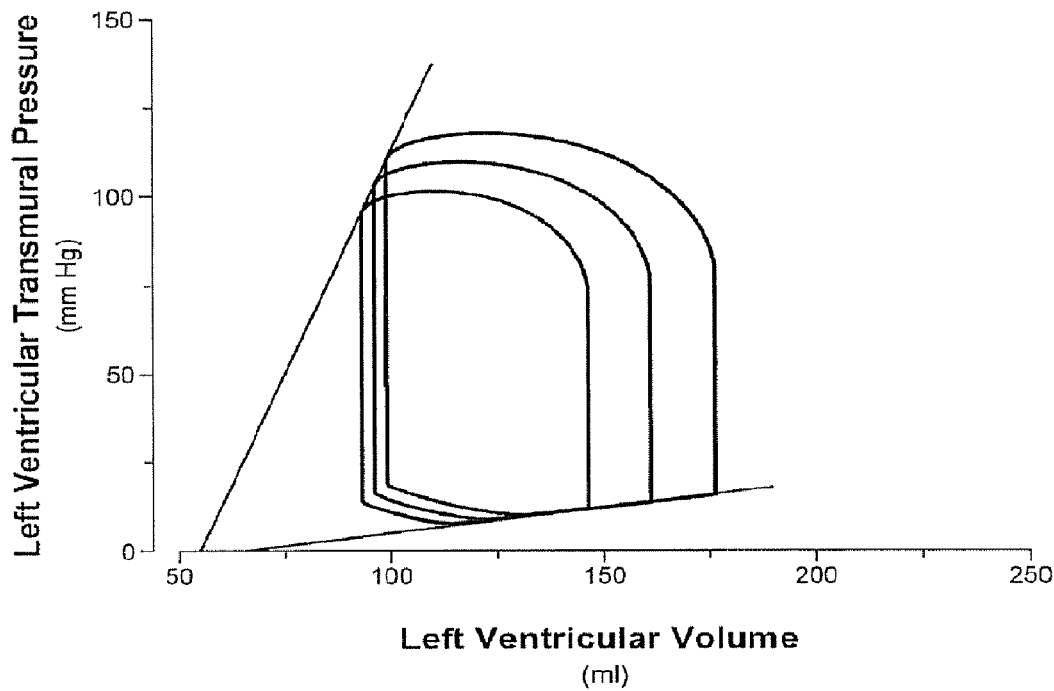
FIG. 3b shows three left ventricular pressure-volume loops for three different loading (pre-load) conditions. Note that the pressures in this figure are measured with respect to intra-thoracic pressure.

In general, end-diastolic stressed volume is a non-linear function of end-diastolic pressure. Over physiologically normal filling pressures, however, the end-diastolic stressed volume exhibits a fairly linear dependence on end-diastolic pressure, as shown in FIGS. 3a and 3b. One can therefore approximate the end-diastolic stressed volume by the product of the end-diastolic compliance, $C_{ed}$, and the end-diastolic transmural (or filling) pressure, $P_{ed}-P_{th}$.

$$EDV \approx V_{ed}^O + C_{ed} \cdot (P_{ed} - P_{th}) \qquad (\text{EQ. 4})$$

The transmural pressure of a vessel is the difference between a vessel's luminal pressure and the pressure of the medium surrounding the vessel. In the case of thoracic structures, the external pressure is intra-thoracic pressure, $P_{th}$. Expressing the stressed volume as a linear function of end-diastolic pressure is a simplification that holds as long as the heart is not operating close to its elastic limit, i.e., as long as filling pressures are not too high.

The end-systolic volume, ESV, can be expressed analogously as $$ESV = V_{es}^O + V_{es}^S \approx V_{es}^O + C_{es} \cdot (P_{es} - P_{th}) \qquad (\text{EQ. 5})$$

Expressing the end-systolic volume as an affine function of end-systolic pressure is well supported by experimental data, as the curvilinear nature of the end-systolic pressure-volume relationship of the left ventricle normally only becomes appreciable at supra-physiological ventricular pressures.

Ventricular stroke volume, SV, is given by the difference of end-diastolic volume and end-systolic volume:

$$SV = EDV - ESV \approx C_{ed} \cdot (P_{ed} - P_{th}) - C_{es} \cdot (P_{es} - P_{th}) + (V_{ed}^O - V_{es}^O) \qquad (\text{EQ. 6})$$

Ejection fraction, EF, references the stroke volume to the corresponding end-diastolic volume:

$$EF \equiv \frac{SV}{EDV} \approx \frac{C_{ed} \cdot (P_{ed} - P_{th}) - C_{es} \cdot (P_{es} - P_{th}) + V_{ed}^O - V_{es}^O}{V_{ed}^O + C_{ed} \cdot (P_{ed} - P_{th})} \qquad (\text{EQ. 7})$$

Cardiac contractility may be defined as the slope of the ventricular end-systolic pressure volume relationship, as illustrated in FIG. 3a. Thus, the contractility is simply the inverse of the ventricular end-systolic compliance, or the elastance of the ventricle at the end of systole, $E_{es}$:

$$E_{es} \equiv \frac{d}{dV} P \bigg|_{es} = \frac{1}{C_{es}} \qquad (\text{EQ. 8})$$

For a healthy adult, the left-ventricular end-diastolic, left-ventricular end-systolic, and intra-thoracic pressures are approximately 8-10 mmHg, 90-95 mmHg, and −4 mmHg, respectively. The left-ventricular end-diastolic compliance is about 10 ml/mmHg, whereas the left-ventricular end-systolic compliance is about 0.4 ml/mmHg. Estimates of the left-ventricular unstressed volume range from 15 ml to 50 ml. These numbers lead to a normal end-diastolic volume of 130-180 ml, an end-systolic volume of 50-80 ml, a stroke volume of about 80 ml, and a normal ejection fraction of 60-70%, all for the left ventricle.

Rearranging (EQ. 3) and (EQ. 4), one may express the end-diastolic and end-systolic compliances in terms of the ventricular volumes and pressures $$C_{ed} = \frac{EDV - V_{ed}^O}{P_{ed} - P_{th}} \text{ and } C_{es} = \frac{ESV - V_{es}^O}{P_{es} - P_{th}} \qquad (\text{EQ. 9})$$

Generalizing these expressions, one can describe the instantaneous pumping action of a ventricle through a time-varying compliance, C(t), by computing the ratio $$C(t) \equiv \frac{V(t) - V^O(t)}{P(t) - P_{th}(t)} \qquad (\text{EQ. 10})$$

where P(t), V(t), and $V^O(t)$ are the instantaneous ventricular pressure, total ventricular volume, and unstressed ventricular volume, respectively. It has been shown that the time-varying compliance so defined is fairly independent of the arterial blood pressure, or 'afterload', against which the heart has to pump, thus serving as a 'load-independent' characterization of cardiac pump function.

Figure 4A:
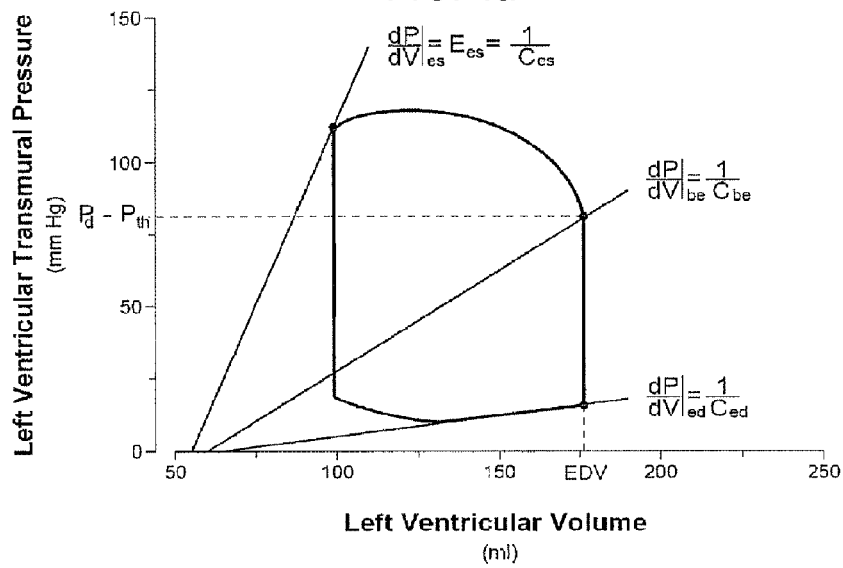
FIG. 4a shows a graph of a left ventricular pressure-volume loop indicating aortic valve opening. Note that the pressures in this figure are measured with respect to intra-thoracic pressure.

The instantaneous, time-varying elastance, E(t), is commonly used instead of the time-varying compliance. E(t) is just the inverse of C(t), that is E(t)=1/C(t). (EQ. 3) evaluates the end-diastolic volume at the beginning of the isovolumic contraction phase, i.e. at the end of ventricular diastole. Likewise, one can compute the end-diastolic volume at the end of the isovolumic contraction phase, or the moment just before ejection from the left ventricle starts with the opening of the aortic valve. This point is illustrated in FIG. 4a, labeled with the subscripts 'be', meaning 'before ejection' (also referred to as pre-ejection in this application). Using the definition of the before-ejection or pre-ejection compliance in accordance with (EQ. 10), one can thus write the end-diastolic volume according to:

$$EDV \approx V_{ed}^O + C_{ed} \cdot (P_{ed} - P_{th}) = V_{be}^O + C_{be} \cdot (P_{be} - P_{th}) \quad \text{(EQ. 11)}$$

Note that, as discussed below, diastolic arterial pressure (DAP) or $P_d$, is a good surrogate for $P_{be}$. (Note that in this application, Applicants use LVEDV to denote left-ventricular end diastolic volume; however, Applicants on occasion omit the "LV".)

In preferred embodiments, Applicants have recognized several physiological approximations that help make tractable the estimation of ejection fraction, end-diastolic volume, and contractility. Applicants have already invoked two important approximations by replacing the end-diastolic and end-systolic stressed volumes by the products of the appropriate compliances and transmural pressures. Two further approximations seem justifiable from a physiological standpoint. First, Applicants will replace the time-varying intra-thoracic pressure by its mean value; second, Applicants will assume that the difference in end-systolic and end-diastolic unstressed volumes does not vary on a beat-by-beat basis.

The first approximation pertains to the time-varying nature of intra-thoracic pressure, $P_{th}$. Mean intra-thoracic pressure is about −4 mmHg; variations about this mean drive breathing. During normal, quiet breathing intra-thoracic, pressure drops to about −6 mmHg over the inspiratory phase of the respiratory cycle and rises to about −2 mmHg during expiration. To measure intra-thoracic pressure directly, one would have to puncture the ribcage to insert a pressure transducer into the pleural space. This is never done for obvious reasons. One can estimate intra-thoracic pressure from esophageal balloon pressure recordings. Such recordings are not obtained either during standard medical care as they would require the rather unpleasant placement of an esophageal balloon catheter. In the discussion that follows, Applicants do not invoke a measurement or estimate of time-varying intra-thoracic pressure.

Normal respiratory frequency is about 12 breaths/minute while a normal heart rate is between 70 and 80 beats/min, which means that there are about six cardiac cycles over the duration of one respiratory cycle. Echocardiographic evaluations of stroke volume and ejection fraction usually average the end-systolic and end-diastolic volume estimates over several cardiac cycles. Furthermore, the estimation algorithm to be developed below do the same, namely average information from several beats to calculate a single estimate of stroke volume, ejection fraction, end-diastolic volume, and contractility. It therefore seems justifiable to replace the time-varying intra-thoracic pressure by a nominal value of its mean, $\overline{P}_{th}$, over the respiratory cycle:

$$P_{th} = \overline{P}_{th} \quad \text{(EQ. 12)}$$

which—without loss of generality—Applicants assume to be −4 mmHg. The equations for stroke volume and ejection fraction therefore take on the form $$SV = C_{ed} \cdot (P_{ed} - \overline{P_{th}}) - C_{es} \cdot (P_{es} - \overline{P_{th}}) + (V_{ed}^O - V_{es}^O) \quad \text{(EQ. 13)}$$

$$EF = \frac{C_{ed} \cdot (P_{ed} - \overline{P_{th}}) - C_{es} \cdot (P_{es} - \overline{P_{th}}) + (V_{ed}^O - V_{es}^O)}{V_{ed}^O + C_{ed} \cdot (P_{ed} - \overline{P_{th}})} \quad \text{(EQ. 14)}$$

The second approximation pertains to the time-varying cardiac unstressed volumes. A chamber's unstressed volume attains its maximum at the end of its filling phase and its minimum during the chamber's peak contraction. The unstressed volume of the canine right ventricle, for example, differs by about 8 ml between diastole (25 ml) and peak systole (17 ml) [1].

Cardiac unstressed volumes cannot be measured directly as this would require arresting the heart once in systole and once in diastole. The contractile state of the arrested heart, however, is an ill-defined concept as the state of myocardial contraction cannot be preserved in the stopped heart. The unstressed volumes are therefore estimated by determining the (linear) end-systolic and end-diastolic pressure-volume relationships and extrapolating these lines to zero transmural pressure (see FIGS. 3a and 3b). However, measuring ventricular volumes with a reasonable degree of precision is a difficult task and extrapolation from such uncertain data transmits the uncertainties to the estimates of unstressed volume. It is not surprising, then, that the difference in end-systolic and end-diastolic unstressed volumes is beyond what current experiments can resolve.

Quite possibly, the cardiac end-systolic and end-diastolic unstressed volumes fluctuate on a beat-by-beat basis (much like the unstressed volume of the systemic veins are subject to sympathetically-driven fluctuations) and thus contribute to stroke volume to a varying degree from one beat to the next. Since current technology cannot resolve such fluctuations, Applicants assume the end-systolic and end-diastolic unstressed volumes of the left ventricle to be constant:

$$V_{ed}^O = \overline{V}_{ed}^O = Q_d \text{ and } V_{es}^O = \overline{V}_{es}^O \quad \text{(EQ. 15)}$$

In this application, Applicants also use the notation $Q_d$ for end-diastolic unstressed volume of the left ventricle.

The expressions for stroke volume and ejection fraction are then given by:

$$SV \approx C_{ed} \cdot (P_{ed} - \overline{P_{th}}) - C_{es} \cdot (P_{es} - \overline{P_{th}}) + (\overline{V}_{ed}^O - \overline{V}_{es}^O) \quad \text{(EQ. 16)}$$

$$EF \approx \frac{C_{ed} \cdot (P_{ed} - \overline{P_{th}}) - C_{es} \cdot (P_{es} - \overline{P_{th}}) + (\overline{V}_{ed}^O - \overline{V}_{es}^O)}{V_{ed}^0 + C_{ed} \cdot (P_{ed} - \overline{P_{th}})} \quad \text{(EQ. 17)}$$

Finally, Applicants make use of (EQ. 11) to express the end-diastolic volume in terms of the 'before ejection' or 'pre-ejection' pressure, compliance, and unstressed volume:

$$SV \approx C_{be} \cdot (P_{be} - \overline{P_{th}}) - C_{es} \cdot (P_{es} - \overline{P_{th}}) + \Delta \overline{V}^O \quad \text{(EQ. 18)}$$

$$EF \approx \frac{C_{be} \cdot (P_{be} - \overline{P_{th}}) - C_{es} \cdot (P_{es} - \overline{P_{th}}) + \Delta \overline{V}^O}{Q_d + C_{be} \cdot (P_{be} - \overline{P_{th}})} \quad \text{(EQ. 19)}$$

where Applicants have introduced the short-hand notation $\Delta \overline{V}^O \equiv \overline{V}_{be}^O - \overline{V}_{es}^O$.

Linear Least-Squares Estimation Algorithm and Calibration Methods

With these approximations in place, Applicants have developed an estimation method for ejection fraction, end-diastolic volume, and cardiac contractility.

In some embodiments, Applicants assume access to beat-by-beat estimates of stroke volume, or actual or true reference measurements of stroke volume, which Applicants will label by their beat number as {SV[1], SV[2], ..., SV[k], ...} [3, 4]. In preferred embodiments, Applicants may require an arterial blood pressure signal from which to extract beat-by-beat estimates of the central aortic pressure at aortic valve closure, $P_{es}[i]$, and when the aortic valve opens, $P_d[i]$. In preferred embodiments, Applicants also assume mean intrathoracic pressure to be constant at −4 mmHg.

In some embodiments, from three or more beats of data, Applicants are able to estimate the end-systolic and the before-ejection compliances and the difference in the unstressed volumes of the left ventricle according to (where ^ denotes "estimate"):

$$S\hat{V}[i] = C_{be} \cdot (P_d[i] - \overline{P}_{Th}) - C_{es} \cdot (P_{es}[i] - \overline{P}_{th}) + \Delta \overline{V}^O \quad (EQ.~20)$$

where Applicants have replaced the pressure $P_{be}$ by the diastolic arterial pressure $P_d$. Stacking up beat-by-beat estimates for stroke volume, Applicants may write the estimation problem in matrix-vector notation and cast it in a least-squares framework over a window of n beats:

$$\begin{bmatrix} P_d[i] - \overline{P}_{th} & -P_{es}[i] + \overline{P}_{th} & 1 \\ \vdots & \vdots & \vdots \\ P_d[i+n] - \overline{P}_{th} & -P_{es}[i+n] + \overline{P}_{th} & 1 \end{bmatrix} \begin{bmatrix} C_{be} \\ C_{es} \\ \Delta \overline{V}^0 \end{bmatrix} = \begin{bmatrix} S\hat{V}[i] \\ \vdots \\ S\hat{V}[i+n] \end{bmatrix} \quad (EQ.~21)$$

In one embodiment, by solving this set of equations Applicants implicitly assume that the compliances $C_{be}$ and $C_{es}$ and the difference in unstressed volumes $\Delta V^O$ remain constant over the window of length n.

The inverse of the estimated end-systolic compliance, i.e. $1/\hat{C}_{es}$, may be thought of as Applicants' estimate of cardiac contractility.

In an embodiment, Applicants may use the estimate $\overline{C}_{be}$ and a single calibration measurement of EF to determine the before-ejection or pre-ejection unstressed volume of the left ventricle according to:

$$EF[j] \cdot [\overline{V_{be}^O} + \hat{C}_{be} \cdot (P_d[j] - \overline{P}_{th})] = S\hat{V}[j] \quad (EQ.~22)$$

Relying on a single calibration makes the single calibration measurement of ejection fraction particularly important. Ideally, one should strive for a robust estimate of $V_{be}^O$ by acquiring several measurements of ejection fraction and solving the resultant set of linear equations in a least-squares manner. Estimating the unstressed volume from multiple calibration measurements thus takes the form $$\begin{bmatrix} EF[j] \\ \vdots \\ EF[j+m] \end{bmatrix} \overline{V}_{be}^0 = \begin{bmatrix} S\hat{V}[j] - \hat{C}_{be} \cdot EF[j] \cdot (P_d[j] - \overline{P}_{th}) \\ \vdots \\ S\hat{V}[j+m] - \hat{C}_{be} \cdot EF[j+m] \cdot (P_d[j+m] - \overline{P}_{th}) \end{bmatrix} \quad (EQ.~23)$$

The estimate $$\hat{V}_{be}^0$$

enables us to get beat-by-beat estimates of end-diastolic volume (EDV) or left-ventricular end-diastolic volume (LVEDV):

$$E\hat{D}V[k] = \hat{V}_{be}^O + \hat{C}_{be} \cdot (P_d[k] - \overline{P_{th}}) \quad (EQ.~24)$$

and ejection fraction:

$$E\hat{F}[K] = \frac{S\hat{V}[k]}{E\hat{D}V[k]} \quad (EQ.~25)$$

The estimation problems outlined above will yield stable results as long as the coefficient matrix on the left-hand-side of (EQ. 21) is well-conditioned, which is the case if the end-systolic pressure $P_{es}$ and the diastolic arterial pressure $P_d$ vary to some degree independently of each other. If the coefficient matrix has approximate column rank 2 (rather than 3), Applicants can try to improve the estimation of the compliances by assuming a constant difference in unstressed volumes and subtracting $\Delta V^O$ from the stroke volume values on the right-hand-side of (EQ. 21), thus turning a poorly-conditioned three-parameter estimation problem into a better-conditioned two-parameter estimation problem. A particular case of such a manipulation presents itself in the special case of $\Delta V^O = 0$. The coefficient matrix on the left-hand-side of (EQ. 23) is by definition well conditioned as it is simply a column vector.

The formalism presented in this section can be applied directly if one has a high-fidelity blood pressure recording taken from the root of the aorta. In such recordings, one can usually identify the dichrotic notch, which is a short-duration, high-frequency oscillation generated by aortic valve closure. The dichrotic notch pressure represents $P_{es}$, the pressure at the end of the systolic ejection period. Such recordings are never made during routine patient management. Unfortunately, the dichrotic notch is not discernible in blood pressure recordings made in the periphery due to the low-pass filter nature of the arterial tree. Finally, the morphology of the arterial blood pressure pulse undergoes significant changes from the aortic root to the peripheral arteries; the diastolic and systolic pressures measured peripherally are respectively lower and higher as their counterparts measured centrally.

In order to implement the estimation method outlined above, one has to solve two problems, namely one has to determine the (central aortic) pressure at aortic valve closure from a peripheral arterial blood pressure recording and one has to determine the degree to which diastolic arterial blood pressure measured peripherally agrees with diastolic aortic blood pressure.

To determine how well peripheral diastolic arterial blood pressure tracks central aortic diastolic pressure, Applicants identified diastolic pressures on a beat-by-beat basis in a pig model using a porcine data set [3] in which Applicants had access to an aortic pressure signal (most likely taken at the level of the descending thoracic aorta), a "radial" artery pressure signal, and a femoral artery pressure signal. The correlations between the peripheral diastolic pressures and the aortic diastolic pressure are excellent with correlation coefficients of 0.995 and 0.981, respectively, which indicates that over a fairly wide range the two diastolic pressures are linearly related.

Figure 5:
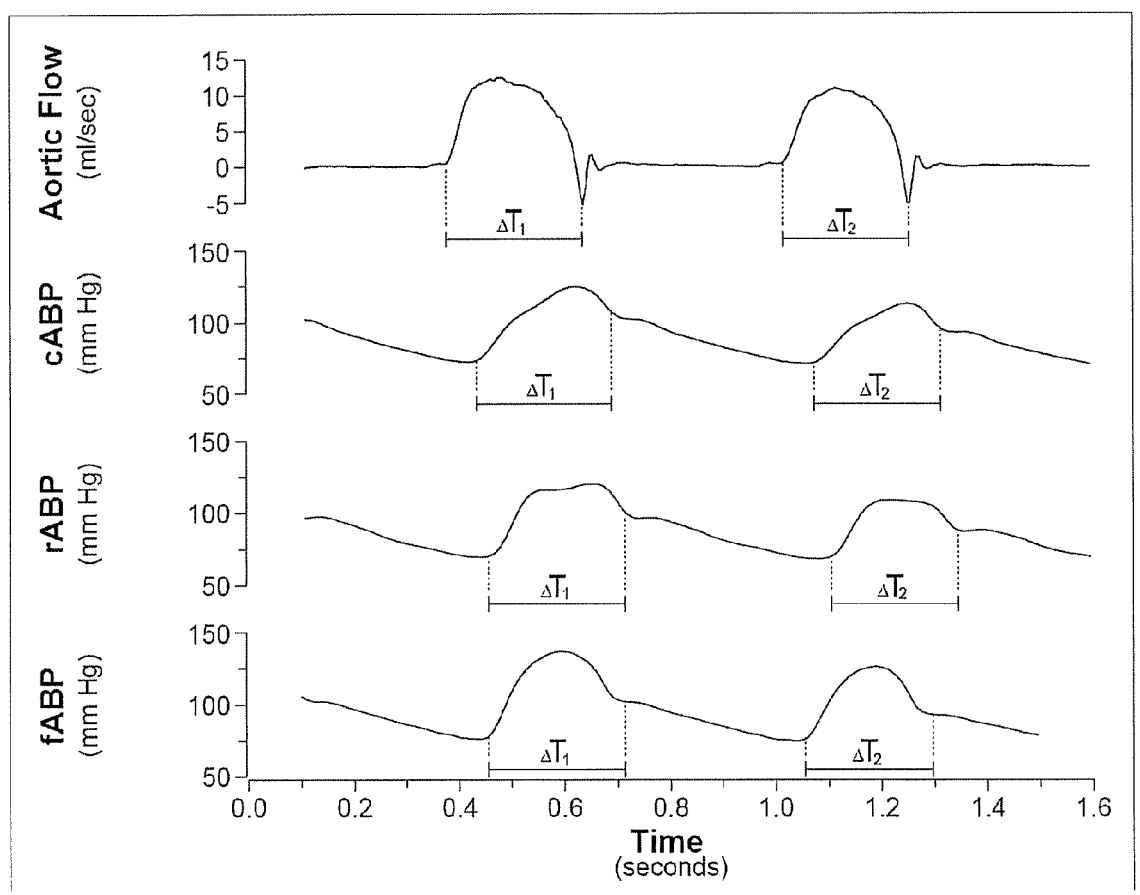
FIG. 5 shows a graph of the relative timing of aortic flow waveforms (top), central aortic pressure (cABP), radial artery pressure (rABP), and femoral artery pressure (fABP) obtained from a porcine animal experiment data set.

Furthermore, in preferred embodiments, Applicants propose to estimate the central aortic pressure at the moment of aortic valve closure from a peripheral arterial pressure waveform, using the strategy illustrated in FIG. 5. Using beat-by-beat measurements or estimates of the ejection period, $\Delta T_i$, Applicants determine the pressure value of the peripheral arterial pressure waveform measured a period $\Delta T_i$ after the onset of the systolic portion of the i-th pressure wavelet. Applicants take the pressure so determined as the i-th beat's estimate for central aortic end-systolic pressure.

Several strategies suggest themselves immediately to measure or to estimate the sequence of ejection periods. First, having access only to the blood pressure recording, one might assume that a particular beat's ejection period is directly related to that beat's duration. The functional form of such a relationship may be established through population studies. Having access to a simultaneous recording of ECG and arterial blood pressure, one might estimate the ejection period by the QT-interval. Since the ejection of blood from the heart occurs during cardiac excitation and subsequent relaxation, the QT-interval might be a sufficiently accurate surrogate for the actual ejection period. In this approach one would be estimating a parameter that is determined by the mechanical coupling of the ventricle to the arterial tree on the basis of electrical events that are occurring purely at the level of the cardiac myocytes. One might therefore expect the correspondence between ejection period and QT-interval to be variable. Finally, if one has access to recordings of heart sounds on a beat-by-beat basis, one can directly measure the ejection period by appropriately identifying aortic valve opening (heart sound $S_1$) and aortic valve closure (heart sound $S_2$).

ADDITIONAL EMBODIMENTS

Other variants of Applicants' proposed methods and systems will now be described.

Figure 4B:
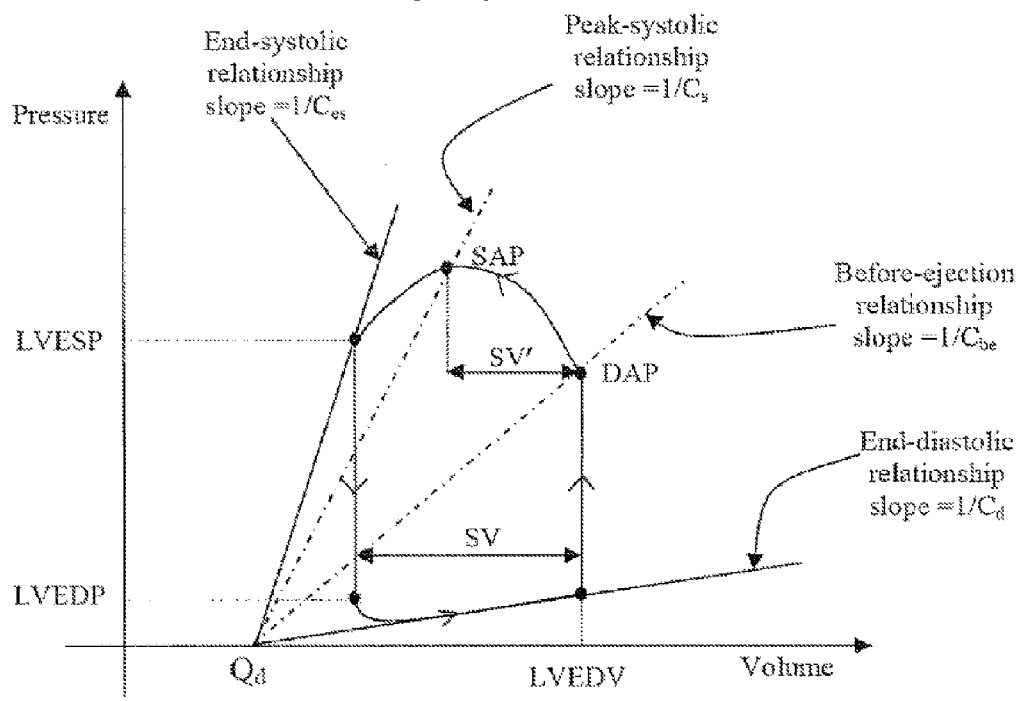
FIG. 4b shows a left ventricular pressure-volume loop showing the straight lines defining the end-diastolic, pre-ejection (or before-ejection), peak-systolic, and end-systolic compliances, as well as systolic arterial blood pressure (SAP), diastolic arterial blood pressure (DAP), preload or left ventricular end-diastolic pressure (LVEDP), and afterload or left ventricular end-systolic pressure (LVESP). Note that the pressures in this figure are measured with respect to intrathoracic pressure.

For instance, in one embodiment, as can be seen with reference to FIG. 4b, Applicants may compute ejection fraction as follows:

$$EF = \frac{SV}{EDV} = \frac{C_{be}(P_d - P_{th}) - C_{es}(P_{es} - P_{th})}{\overline{V}_{ed}^0 + C_{be}(P_d - P_{th})} \quad \text{(EQ. 26)}$$

where stroke volume is given by:

$$SV = C_{be}(P_d - P_{th}) - C_{es}(P_{es} - P_{th}) \quad \text{(EQ. 27)}$$

Note the prominence of both $\overline{V}_{ed}^0$ (end-diastolic unstressed volume) and intra-thoracic pressure, $P_{th}$, in (EQ. 26). (Note that in FIG. 4b, the label LVESP is $P_{es}$, LVEDP is $P_d$, and $Q_d$ is $\overline{V}_{ed}^0$.) The intra-thoracic pressure variations during the respiratory cycle modulate left-ventricular and arterial blood pressures, LVP and ABP, respectively, and cause beat-to-beat variations in SV, which in turn cause beat-to-beat variations in EF [3].

Note that peak-systolic pressure is denoted $P_s$ and end-diastolic pressure is denoted $P_d$.

In one embodiment, Applicants assume $P_{th}=0$ (see FIG. 4b), and approximate stroke volume (where ' denotes an approximation) by:

$$SV' = C_{be}P_d - C_sP_s \quad \text{(EQ. 28)}$$

and thus EF simplifies to:

$$EF' = \frac{SV'}{EDV'} = \frac{C_{be}P_d - C_sP_s}{\overline{V}_{ed}^0 + C_{be}P_d}, \quad \text{(EQ. 29)}$$

and EDV is approximated by:

$$EDV' \approx C_{be}P_d. \quad \text{(EQ. 30)}$$

Given beat-to-beat measurements of SAP or $P_s$, DAP or $P_d$, and SV and assuming a nominal value for $\overline{V}_{ed}^0$ (or $Q_d$), Applicants then use (EQ. 28) to compute beat-to-beat estimates of $C_{be}$ and $C_s$ to continuously estimate beat-to-beat EF from the ABP waveform using (EQ. 29). Furthermore, given beat-to-beat estimates of $C_{be}$ and $P_d$ or DAP, (EQ. 30) can be used to estimate EDV.

However, Applicants note that SV' does not in general equal SV (though Applicants believe SV' may be proportional to SV), leading to bias errors in the estimates of $C_{be}$ and $C_s$.

Note that if an estimate of actual SV is not available, one can use a proportional estimate of SV, e.g., $$\frac{SV}{C_a},$$

where $C_a$ is lumped aortic or arterial compliance, such that (EQ. 28) reduces to:

$$\frac{SV'}{C_a} = \frac{C_{be}}{C_a}P_d - \frac{C_s}{C_a}P_s \quad \text{(EQ. 31)}$$

and approximate EF is computed using:

$$EF' \approx \frac{\frac{C_{be}}{C_a}P_d - \frac{C_s}{C_a}P_s}{\frac{\overline{V}_{ed}^0}{C_a} + \frac{C_{be}}{C_a}P_d}, \quad \text{(EQ. 32)}$$

from which the proportionality constant $C_a$ cancels out [3]. Note that one now has to assume a nominal value for $$\frac{\overline{V}_{ed}^0}{C_a}$$

in (EQ. 32), and that to obtain EDV', one needs to perform a calibration as well.

Estimation Using a Linear Least-Squares Error Criterion

In doing EF estimation from (EQ. 25), Applicants assume that $C_{be}$ and $C_s$ vary slowly from beat-to-beat. Thus, Applicants ensure that the window size in our linear least-squares estimation scheme does not exceed half a minute (30 beats at a heart rate of 60 beats/min), which is probably slightly larger than the timescale on which $C_{be}$ and $C_s$ change. Applicants estimated EF directly from (EQ. 25) by computing least-squares estimates of $C_{ben}$, and $C_{sn}$, over a fixed-length data window, i.e., Applicants calculated least-squares estimates of $C_{ben}$, and $C_{sn}$, for the $n^{th}$ cardiac beat using a window comprising every $m^{th}$ beat of the b/2 adjacent beats on each side of this beat, so as to obtain a well-conditioned estimation scheme. In other embodiments, Applicants use every beat of the b/2 adjacent beats on each side of this beat. This results in a total of $$\frac{b}{2m}$$

(even) equations in two unknowns, leading to a reasonably well-conditioned least-squares estimation problem:

$$\begin{bmatrix} P_{sn} & P_{dn} \\ \vdots & \vdots \\ P_{s(b+n)} & P_{d(b+n)} \end{bmatrix} \begin{bmatrix} C_{be\left(n-1+\frac{b}{2}\right)} \\ C_{s\left(n-1+\frac{b}{2}\right)} \end{bmatrix} = \begin{bmatrix} SV_n \\ \vdots \\ SV_{b+n} \end{bmatrix} \quad (EQ.\ 33)$$

where Applicants estimated absolute SV estimates using the CO estimation method of Parlikar et al. described in co-pending, commonly-owned U.S. patent application Ser. No. 12/121,042, the contents of which are incorporated herein in their entirety. The derivation presented here does not change if Applicants use proportional SV estimates, i.e., $$\frac{SV_n}{C_a},$$

instead of absolute SV estimates.

Furthermore, Applicants assign the estimated $C_{ben}$ and $C_{sn}$ from each window to the midpoint of that window, and assume that in (EQ. 33), $$n > \frac{b}{2m},$$

such that ejection fraction in the $n^{th}$ cardiac cycle, $EF_n$, is given by:

$$EF_n = \frac{SV_n'}{EDV_n'} = \frac{C_{ben}P_{dn} - C_{sn}P_{sn}}{\overline{V}_{edn}^0 + C_{ben}P_{dn}} \quad (EQ.\ 34)$$

and estimated EDV in the $n^{th}$ cycle, $EDV'_n$ is given by:

$$EDV'_n \approx C_{ben}P_{dn}. \quad (EQ.\ 35)$$

It is important to note that Applicants could use the definition of SV from (EQ. 20) or (EQ. 28) above in the method of Parlikar et al. described in co-pending, commonly-owned U.S. patent application Ser. No. 12/121,042. This would result in an attempt to, in the case of (EQ. 20) and neglecting intra-thoracic pressure, compute beat-to-beat estimates of $C_{be}$, $C_{es}$, and $\tau$ in a three-parameter linear least-squares estimation scheme of the form:

$$\frac{\Delta P_n}{T_n} + \frac{\overline{P}_n}{T_n} = \frac{C_{ben}P_{dn}}{T_n} - \frac{C_{esn}P_{esn}}{T_n} \quad (EQ.\ 36)$$

where $T_n$ is the duration of the $n^{th}$ cardiac cycle or beat, $C_{ben}$ and $C_{esn}$ are the before-ejection and end-systolic compliances in the $n^{th}$ cardiac cycle, $P_{dn}$ is the diastolic arterial blood pressure in the $n^{th}$ cardiac cycle, $P_{sn}$ is the peak-systolic arterial blood pressure in the $n^{th}$ cycle, $\Delta P_n$ is the beat-to-beat pressure change at the beat (or cycle) onset times $t_n$ and $t_{n+1}$ [defined in (EQ. 43) below], and $\Delta \overline{P}_n$ is the mean arterial blood pressure in the $n^{th}$ cardiac cycle. Such a scheme, however, may turn out to be severely ill-conditioned, as there might be an insufficient degree of variability in the data to estimate all three parameters simultaneously. In addition, this approach would also suffer from the modeling assumption above, namely that SV' does not in general equal SV, leading to bias errors in the estimates of $C_{be}$ and $C_s$.

Calibration Methods for EF and EDV in (EQ. 34) and (EQ. 35)

The formulae for EF and EDV in (EQ. 34) and (EQ. 35) seem to require no calibration to true or reference measurements. Once $C_{ben}$ and $C_{sn}$ are estimated, the only unknown in (EQ. 34) is $\overline{V}_{ed}^0$, for which one may assume a nominal value.

However, there are three problems with this approach, though, and Applicants list them here in order of importance. First, as mentioned above, SV' does not equal SV (though Applicants believe SV' may be proportional to SV), leading to bias errors in the estimates of $C_{be}$ and $C_s$. Second, it is difficult to assume a good value for $\overline{V}_{ed}^0$, as it can vary from between 5 ml to 200 ml depending on ventricular disease state. Third, because Applicants are assuming $P_{th}=0$ and using (EQ. 28) to estimate SV based on $P_s$ or SAP and $P_d$ or DAP, instead of $P_{es}$ or ESP and $P_{ed}$ or EDP, respectively, there will be an additional component to the bias errors in our estimates of $C_{be}$ and $C_s$, and thus, in our EF and EDV estimates.

To attempt to correct for these bias errors, Applicants use a constant calibration factor to relate estimated and reference EF or EDV, such that our estimate of EF in the $n^{th}$ cardiac cycle, $EF_n$, is given by:

$$EF_n = \delta \frac{SV_n'}{EDV_n'} = \delta \frac{C_{ben}P_{dn} - C_{sn}P_{sn}}{\overline{V}_{edn}^0 + C_{ben}P_{dn}} \quad (EQ.\ 37)$$

and the estimate of EDV in the $n^{th}$ cardiac cycle, $EDV'_n$, is given by:

$$EDV'_n \approx \epsilon \cdot C_{ben} P_{dn}. \quad (EQ.\ 38)$$

Applicants could select the constants $\delta$ or $\epsilon$ to minimize the RMSNE between the true and estimated EF (or EDV). However, in this section, Applicants use two types of calibration: mean and single-point calibration. In mean calibration, Applicants set $\delta$ (or $\epsilon$) to be the ratio of the mean of the reference EF (or EDV) to the mean of the estimated EF (or EDV) waveform. In single-point calibration, Applicants set $\delta$ (or $\epsilon$) to be the ratio of a single reference EF (or EDV) point to the corresponding point in the estimated EF (or EDV) waveform.

RMSNE Error Criterion

In evaluating the goodness-of-fit of our calibrated EF or EDV estimates, i.e., to compare reference EF or EDV to estimated EF or EDV, Applicants used the root-mean-square-normalized-error criterion. For a particular record s, given $n_s$ points at which EF (or EDV) was measured and estimated, the RMSNE (in %) for the EF (or EDV) for record s, denoted $RMSNE_s$, is given by:

$$RMSNE_s = \sqrt{\frac{1}{n_s} \sum_{n=1}^{n^s} \left( \frac{100(\text{True } X_n - \text{Estimated } X_n)}{\text{True } X_n} \right)^2}. \quad (EQ.\ 39)$$

where X denotes either EF or EDV.

Within a data set, records typically contain varying numbers of reference EF or EDV measurements, and thus the aggregate RMSNE over all records is calculated as the weighted mean of the individual RMSNEs. Assuming that there are a total of $N_S$ reference measurements, the aggregate RMSNE is given by:

$$\text{Aggregate } RMSNE = \sqrt{\frac{1}{N_S} \sum_s n_s (RMSNE_s^2)}. \quad \text{(EQ. 40)}$$

A Naive Sample and Hold Estimator

For the animal (canine) experiment data set discussed below, since Applicants only had intermittent echocardiography-based EF (or LVEDV) measurements, Applicants used the following sample-and-hold naïve estimator given by:

$$SHX_{n+1} = \text{True}X_n, \quad \text{(EQ. 41)}$$

where $n \geq 2$, SH $X_i$=True $X_i$, and where X denotes either EF or LVEDV. Again, if the RMSNE for the sample-and-hold naïve estimator is smaller than that of the estimated quantity itself, it implies that our estimate does not add more information than can be obtained by simply holding the value of the previous sample.

Animal (Canine) Data Set

The animal (canine) experiment data set was the result of a study on three beagles (weighing 10-15 kg) approved by the Michigan State University All-University Committee on Animal Use and Care. Dog 1 was intubated under anesthesia and mechanically ventilated. Once intubated, the dog underwent a thoracotomy and an aortic flow transducer was placed. This dog was allowed ten days to recover from this major surgery.

The same experimental protocol was then performed on each of the three dogs: one with the chronic instrumentation described above, and two others. Each animal was anesthetized, but not mechanically ventilated. Catheters were placed in the thoracic aorta to measure cABP, and in the femoral artery to measure fABP. A syringe pump catheter was placed into a cephalic vein for drug administration, and ECG leads were placed on the animal. In each animal, over the course of approximately 1 hour, CO, EF, ABP, and HR were varied by one or more of the following interventions: volume infusions, fast hemorrhage, intravenous (IV) drugs (one or more of phenylephrine, nitroprusside, or dobutamine). During the experiment, 2-dimensional echocardiography measurements were intermittently used so as to obtain reference LVEDV, LVESV, and thus, EF measurements.

The table in FIG. 6 summarizes the population statistics for the canine data set. It is important to note that for Dog 3, the variability in HR and mean cABP is particularly small. In fact, the beat-to-beat variability as measured by the beat-to-beat variability index (B2BVI)

$$B2BVI_b = \frac{1}{360} \sum_{n=b}^{b+360} \left(100 \frac{\Delta P_n}{PP_n}\right). \quad \text{(EQ. 42)}$$

where $PP_n$ is pulse pressure in the $n^{th}$ cardiac cycle, and $\Delta P_n$, which was introduced above, i.e., the beat-to-beat pressure change at the beat (or cycle) onset times $t_n$ and $t_{n+1}$, is given by $$\Delta P_n = P(t_{n+1}) - P(t_n) \quad \text{(EQ. 43)}$$

and does not exceed 1% for the entire record for Dog 3, does not exceed 3% for the entire record for Dog 2, and only exceeds 5% for a few windows of data for Dog 1, with most variability seen with the fABP waveform.

For Dog 1, the data set is comprised of measurements of central arterial blood pressure (cABP) measured at the aorta, carotid arterial blood pressure (carABP), and femoral arterial blood pressure (fABP), all sampled at 250 Hz with 16 bit resolution. In addition, there are intermittent echocardiography measurements of heart rate, left ventricular end-systolic volume and left ventricular end-diastolic volume, from which one can compute left ventricular ejection fraction using (EQ. 2).

For Dogs 2 and 3, the data set comprised of measurements of central arterial blood pressure (cABP) measured at the aorta sampled at 250 Hz with 16 bit resolution. Similar to Dog 1, there are intermittent echocardiography measurements of heart rate, left ventricular end-systolic volume (LVESV) and left ventricular end-diastolic volume (LVEDV), from which one can compute left ventricular ejection fraction (EF) using (EQ. 2). There are no peripheral arterial blood pressure waveforms available for Dogs 2 and 3. For Dog 3, Applicants averaged every 3 echocardiography measurements since they were taken very close together.

Using standard open-source algorithms on the cABP waveforms, Applicants derived onset times for each cardiac beat and HR. Applicants calculated systolic and diastolic cABP, and mean cABP for all three dogs. For Dog 1, Applicants also calculated systolic and diastolic carABP, systolic and diastolic fABP, mean carABP, and mean fABP. Applicants computed EF using the intermittent echocardiography measurements. For Dog 3 Applicants averaged every three EF (or LVEDV) measurements as each consecutive set of three measurements was taken at about the same time instant. All the data processing and EF and LVEDV estimation algorithms were implemented in MATLAB™ R14 (Mathworks Inc., Natick, Mass.).

Experimental Results on Ejection Fraction

Applicants first used the available ABP waveforms in the canine data set to estimate beat-to-beat stroke volume using the CO estimation method of Parlikar et al. described in co-pending, commonly-owned U.S. patent application Ser. No. 12/121,042, and then used the estimated SV in the linear least squares estimation scheme (EQ. 33), with a window size of 50 beats and two evenly spaced points per window, to obtain beat-to-beat estimates of $C_{be}$ and $C_s$. Applicants then computed an uncalibrated EF estimate assuming $\nabla_{ed}^0 = 5$ ml, a plausible value for the animals in Applicants' data set [7, 8]. Note that other values of $\nabla_{ed}^0$ could have been used since an error in $\nabla_{ed}^0$ can to some extent be corrected by calibration. Varying $\nabla_{ed}^0$ from 5 to 150 ml only moderately affected the estimation results.

The table in FIG. 7 summarizes the results obtained for a window size of 50 beats (or, approximately half a minute at a HR of 100 bpm) for the cABP, carABP, and fABP waveforms, using a mean calibration. The RMSNEs for the SH EF estimate reflect fairly low EF variability for Dogs 2 and 3. Applicants believe that these low RMSNEs are sufficiently low to make our EF estimation method useful in clinical applications. In addition, the fact that results are reasonable whether Applicants use the cABP, fABP or carABP waveforms for Dog 1 implies that our method could be used in a minimally-invasive manner.

Figure 10:
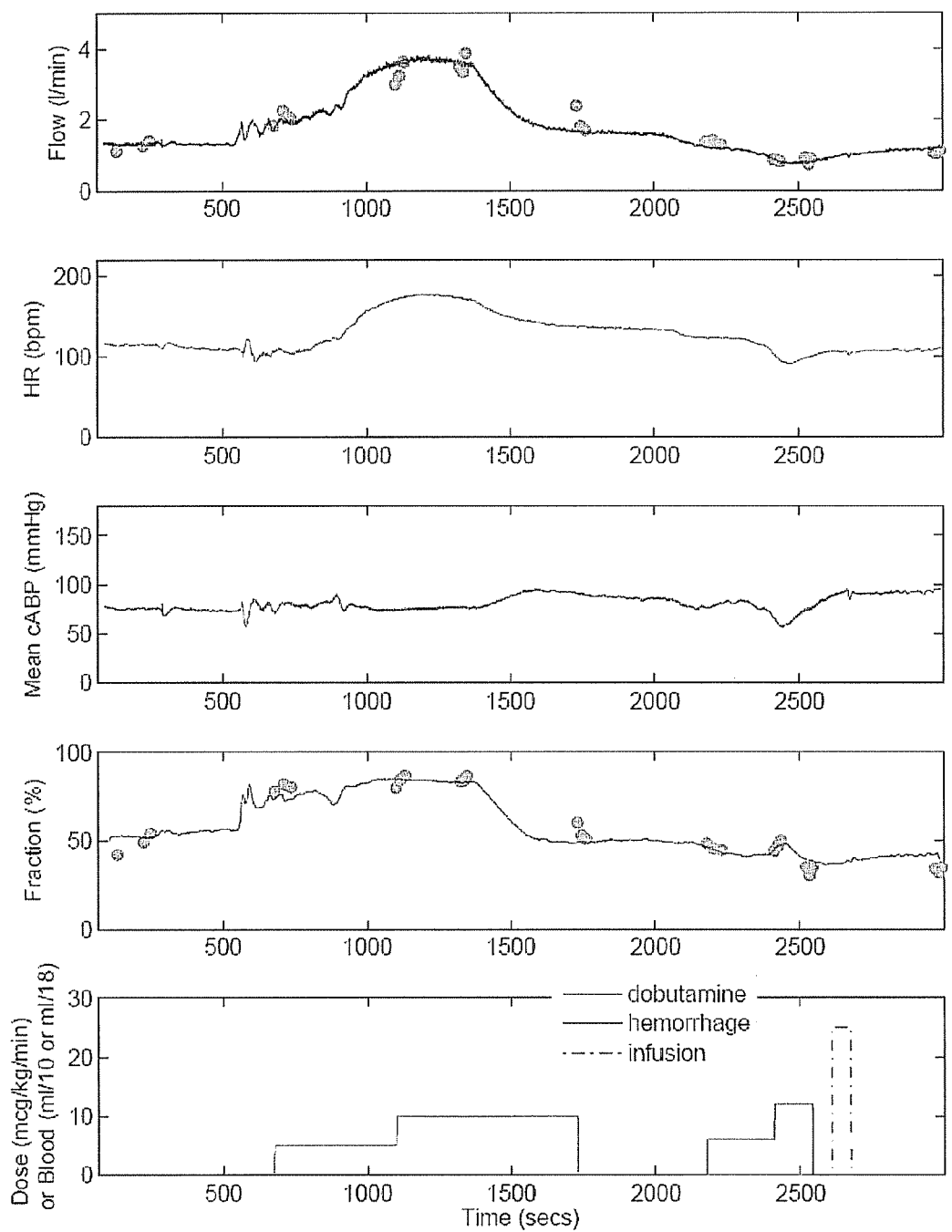
FIG. 10 is a graph of experimental results showing true and estimated CO (using cABP), HR, mean cABP, true and estimated LVEDV (using cABP), and IV drugs for Animal 2 with a mean calibration.

FIG. 10 shows the true and estimated EF for Dog 2 using a mean calibration. Note that the estimated EF tracks the true EF quite well during the infusions of dobutamine, which increases EF by decreasing $C_{es}$, and volume changes (hemorrhage results in a controlled response to lower $C_{es}$, while volume infusion results in a controlled response to increase $C_{es}$).

The table in FIG. 8 summarizes the results obtained for a window size of 50 beats for the cABP, carABP, and fABP waveforms, by performing a single-point calibration using the second EF measurement in each canine record. (In the table, Applicants also list the RMSNEs for the SH EF estimate (EQ. 41) described above.) Applicants believe that these low RMSNEs are sufficiently low to make our estimation method useful in clinical applications, especially given that these results were obtained with only one reference measurement used for calibration. Note that the results in the table in FIG. 8 are reasonable whether Applicants use the cABP, fABP or carABP waveforms for Dog 1, which implies that our method could be used in a minimally-invasive manner.

Figure 11:
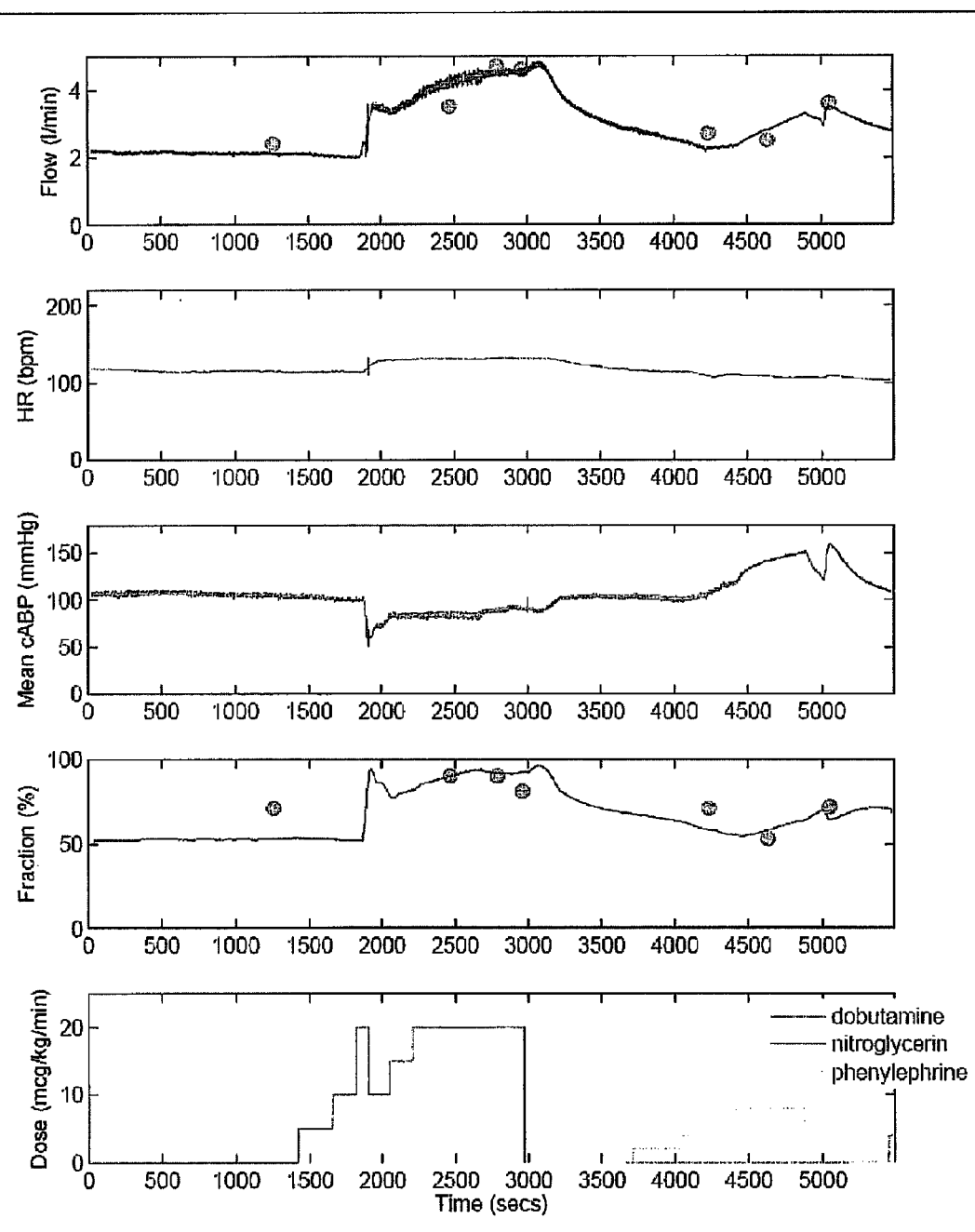
FIG. 11 is a graph of experimental results showing true and estimated CO (using cABP), HR, mean cABP, true and estimated LVEDV (using cABP), and IV drugs for Animal 2 with a single point calibration.

FIG. 11 shows the true and estimated EF for Dog 1 with a single-point calibration (using the second EF measurement). Note that the estimated EF tracks the true EF quite well during the infusions of dobutamine and phenylephrine (which increase EF by decreasing $C_{es}$).

Experimental Results on Left Ventricular End-Diastolic Volume

Using the available ABP waveforms in the canine data set, Applicants obtained beat-to-beat estimates of $C_{be}$, and used these estimates to compute beat-to-beat estimates of LVEDV using (EQ. 38).

The table in FIG. 9 summarizes the results obtained for the cABP, carABP, and fABP waveforms, using a mean calibration. In the table, Applicants also list the RMSNEs for the SH LVEDV estimate (EQ. 41) described above. The RMSNEs for the SH EF estimate reflect very low LVEDV variability for Dogs 2 and 3. Applicants believe that these low RMSNEs are sufficiently low to make our LVEDV estimation method useful in clinical applications. In addition, the fact that results are reasonable whether Applicants use the cABP, fABP or carABP waveforms for Dog 1 implies that our method could also be used in a minimally-invasive manner.

Figure 12:
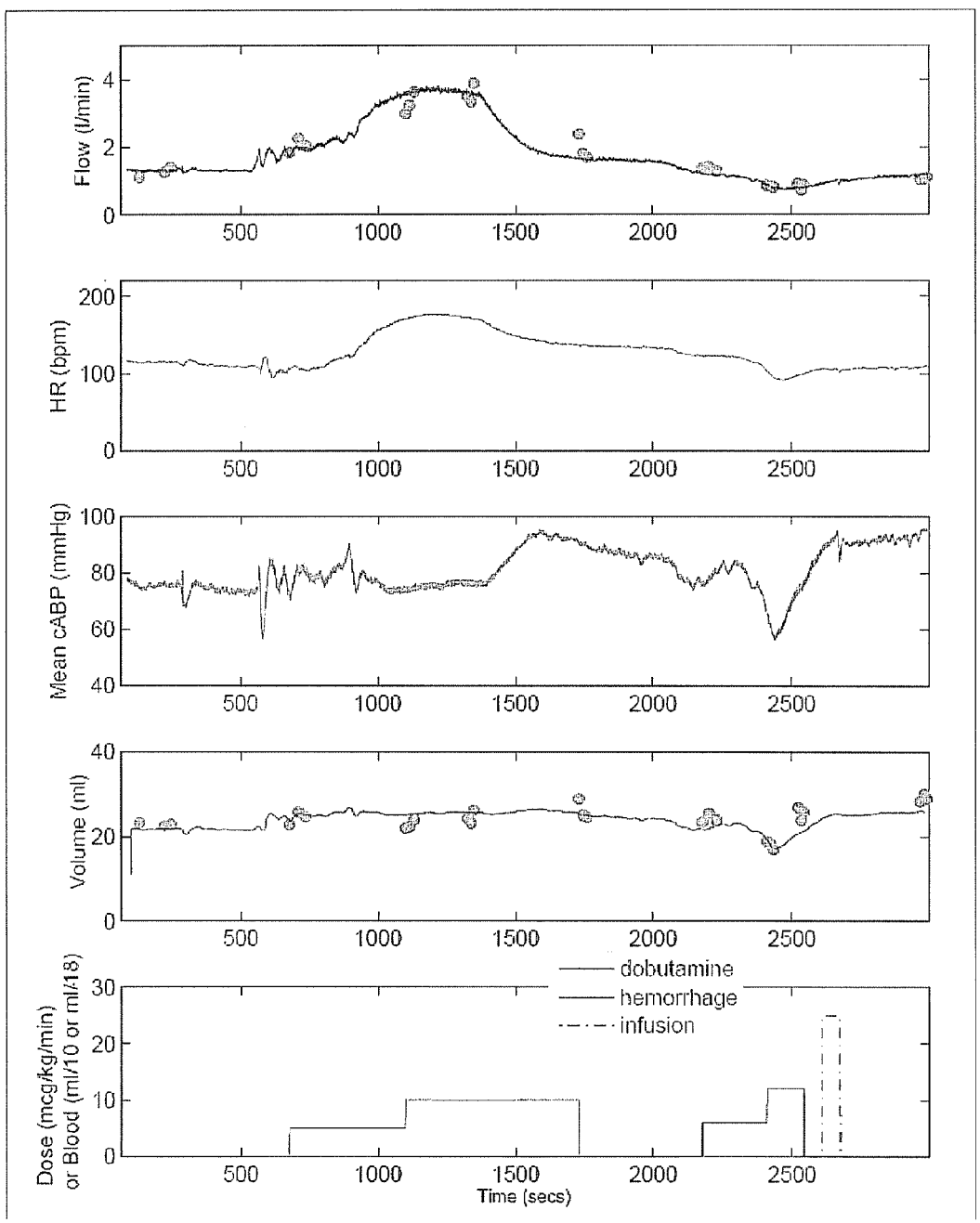
FIG. 12 is a graph of experimental results showing true and estimated CO (using cABP), HR, mean cABP, true and estimated LVEDV (using cABP), and IV drugs for Dog 2 with a mean calibration.

FIG. 12 shows the true and estimated LVEDV for Dog 2 with a mean calibration. One might want to note that the estimated LVEDV tracks the true LVEDV quite well during the infusions of dobutamine (which indirectly increases LVEDV by reducing TPR) and volume changes (hemorrhage results in lower LVEDV, while volume infusion results in higher LVEDV).

The invention may be embodied in other specific forms without departing from the spirit or essential characteristics thereof. The forgoing embodiments are therefore to be considered in all respects illustrative, rather than limiting of the invention.

LIST OF REFERENCES

[1] V.-K. Lau and K. Sagawa. Model analysis of the contribution of atrial contraction to ventricular filling. Annals of Biomedical Engineering, 7:17-201, 1979.

[2] P. Marino. The ICU Book, chapter 9, pages 163-179. Lippincott Williams & Wilkins, Philadelphia, Pa., 3rd edition, 2007.

[3] T. Parlikar. Modeling and Monitoring of Cardiovascular Dynamics for Patients in Critical Care. Doctoral dissertation, Department of Electrical Engineering and Computer Science, Massachusetts Institute of Technology, Cambridge, Mass., June 2007.

[4] T. Parlikar, T. Heldt, G. Ranade, and G. Verghese. Model-based estimation of cardiac output and total peripheral resistance. Computers in Cardiology, 34:379-382, 2007.

[5] G. D. Rubenfeld, E. McNamara-Aslin, and L. Rubinson. The Pulmonary Artery Catheter, 1967-2007: Rest in Peace? JAMA, 298(4):458-461, 2007.

[6] M. Shah, V. Hasselblad, L. Stevenson, C. Binanay, C. O'Conner, G. Sopko, and R. Califf. Impact of the pulmonary artery catheter in critically ill patients Journal of the American Medical Association, 294:1664-1670, 2005.

[7] R. Mukkamala, J. Kuiper, J. Sala-Mercardo, R. Hammond, J.-K. Kim, L. W. Stephenson, and D. S. O'Leary. "Continuous cardiac output and left atrial pressure monitoring by pulmonary artery pressure waveform analysis. Proceedings of the 28$^{th}$ Annual IEEE Engineering in Medicine and Biology Conference, pp. 620-623, September 2006.

[8] G. Swamy, B. Olivier, J. Kuiper, R. Mukkamala. "Continuous ejection fraction estimation by model-based analysis of an aortic pressure waveform: comparison to echocardiography" Proceedings of the 29$^{th}$ Annual IEEE Engineering in Medicine and Biology Conference, pp. 963-966, August 2007.

What is claimed is:

1. A method for estimating beat-by-beat cardiovascular parameters and variables, comprising:
   processing one or more cycles of arterial blood pressure information to determine intra-beat and inter-beat variability in blood pressure; and
   computing estimates of one or more cardiovascular parameters and variables from the intra-beat variability, the inter-beat variability, beat-by-beat estimates of stroke volume, and a ventricular pressure-volume model;
   wherein the cardiovascular parameters and variables include at least one of a beat-by-beat pre-ejection ventricular compliance, a beat-by-beat end-diastolic compliance, a beat-by-beat end-systolic ventricular compliance, and a beat-by-beat peak-systolic compliance, determined for at least one of the left and right ventricle and computing estimates comprises optimization of an error criterion.

2. The method of claim 1, further comprising using information from phonocardiographic measurements.

3. The method of claim 2, wherein the phonocardiographic information includes parameters relating to the beat-by-beat timing of cardiac cycle events.

4. The method of claim 3, wherein the parameters relating to the beat-by-beat timing of cardiac cycle events include a duration of ventricular ejection.

5. The method of claim 1, wherein the at least one of a beat-by-beat pre-ejection ventricular compliance, a beat-by-beat end-systolic ventricular compliance, and a beat-by-beat peak-systolic compliance is estimated over a data window.

6. The method of claim 1, wherein the error criterion is least-squared error.

7. A method for estimating beat-by-beat cardiovascular parameters and variables, comprising:
   processing one or more cycles of arterial blood pressure information to determine intra-beat and inter-beat variability in blood pressure; and
   computing estimates of one or more cardiovascular parameters and variables from the intra-beat variability, the inter-beat variability, beat-by-beat estimates of stroke volume, and a ventricular pressure-volume model, wherein the cardiovascular parameters and variables include an uncalibrated beat-by-beat ejection fraction; and
   computing calibrated beat-by-beat ejection fraction from the uncalibrated beat-by-beat ejection fraction using one or more calibration parameters, wherein the calibration parameters are computed using an optimization criterion.

8. The method of claim 7, wherein the calibration parameters are computed for each of the beats.

9. The method of claim 7, wherein the calibration parameters include ventricular dead volume.

10. The method of claim 7, wherein the calibration parameters include intra-thoracic pressure.

11. The method of claim 7, wherein the cardiovascular parameters and variables include uncalibrated beat-by-beat end-diastolic volume.

12. The method of claim 11, further comprising computing calibrated beat-by-beat end-diastolic volume from the uncalibrated beat-by-beat end-diastolic volume using a second set of calibration parameters.

13. The method of claim 12, wherein the second set of calibration parameters is computed using an optimization criterion.

14. The method of claim 12, wherein the second set of calibration parameters is computed for each of the beats.

15. The method of claim 12, wherein the second set of calibration parameters include ventricular dead volume.

16. The method of claim 12, wherein the second set of calibration parameters include intra-thoracic pressure.

17. The method of claim 1, further comprising computing beat-by-beat cardiac contractility.

18. The method of claim 1, wherein the arterial blood pressure information represents arterial blood pressure is measured at a central artery of the cardiovascular system.

19. The method of claim 18, wherein the central artery is the aorta.

20. The method of claim 1, wherein the arterial blood pressure information represents arterial blood pressure is measured at a peripheral artery of the cardiovascular system.

21. The method of claim 1, wherein the arterial blood pressure information represents arterial blood pressure is measured at a pulmonary artery of the cardiovascular system.

22. The method of claim 1, wherein the arterial blood pressure information represents arterial blood pressure is measured using a noninvasive blood pressure device.

23. The method of claim 22, wherein the arterial blood pressure information represents arterial blood pressure is measured using a photoplethysmographic blood pressure device.

24. The method of claim 22, wherein the arterial blood pressure information represents arterial blood pressure measured using a tonometric blood pressure device.

25. The method of claim 1, wherein processing the one or more cycles of arterial blood pressure includes obtaining a diastolic blood pressure; a peak-systolic blood pressure; and an end-systolic blood pressure for each cycle.

26. The method of claim 25, wherein the end-systolic blood pressure is estimated using an estimate of the duration of ventricular ejection.

27. The method of claim 26, wherein the estimate of the duration of ventricular ejection is obtained using phonocardiographic measurements.

28. The method of claim 1, wherein processing the one or more cycles of arterial blood pressure includes obtaining an onset time for each cycle.

29. The method of claim 1, wherein processing the one or more cycles of arterial blood pressure includes obtaining a beat duration for each cycle.

30. A system for estimating beat-to-beat cardiac output comprising:
a blood pressure measuring device;
a processor;
a display;
a user interface; and
a memory storing computer executable instructions, which when executed by the processor cause the processor to:
receive one or more cycles of arterial blood pressure information from the blood pressure measuring device;
receive beat-to-beat estimates of stroke volume;
analyze one or more cycles of arterial blood pressure information to determine intra-beat and inter-beat variability in blood pressure;
compute estimates of one or more cardiovascular parameters and variables from the intra-beat variability, the inter-beat variability, beat-to-beat estimates of stroke volume, and a ventricular pressure-volume model; and
display the estimates;
wherein the cardiovascular parameters and variables include at least one of a beat-by-beat pre-ejection ventricular compliance, a beat-by-beat end-diastolic compliance, a beat-by-beat end-systolic ventricular compliance, and a beat-by-beat peak-systolic compliance, determined for at least one of the left and right ventricle and computing estimates comprises optimization of an error criterion.

31. The system of claim 30, wherein the computer executable instructions, when executed by the processor, cause the processor to compute the estimates of one or more cardiovascular system parameters and variables using information from phonocardiographic measurements.

32. The system of claim 31, wherein the phonocardiographic information includes parameters relating to the beat-by-beat timing of cardiac cycle events.

33. The system of claim 32, wherein the parameters relating to beat-by-beat timing of cardiac cycle events include a duration of ventricular ejection.

34. The system of claim 30, wherein the at least one of a beat-by-beat pre-ejection ventricular compliance, a beat-by-beat end-systolic ventricular compliance, and a beat-by-beat peak-systolic compliance is estimated over a data window.

35. The system of claim 30, wherein the error criterion is least-squared error.

36. A system for estimating beat-to-beat cardiac output comprising:
a blood pressure measuring device;
a processor;
a display;
a user interface; and
a memory storing computer executable instructions, which when executed by the processor cause the processor to:
receive one or more cycles of arterial blood pressure information from the blood pressure measuring device;
receive beat-to-beat estimates of stroke volume;
analyze one or more cycles of arterial blood pressure information to determine intra-beat and inter-beat variability in blood pressure;
compute estimates of one or more cardiovascular parameters and variables from the intra-beat variability, the inter-beat variability, beat-to-beat estimates of stroke volume, and a ventricular pressure-volume model, wherein the cardiovascular parameters and variables include an uncalibrated beat-by-beat ejection fraction; and
compute calibrated beat-by-beat ejection fraction from the uncalibrated beat-by-beat ejection fraction using one or more calibration parameters, wherein the calibration parameters are computed using an optimization criterion.

37. The system of claim 36, wherein the calibration parameters are computed for each of the beats.

38. The system of claim 36, wherein the calibration parameters include ventricular dead volume.

39. The system of claim 36, wherein the calibration parameters include intra-thoracic pressure.

40. The system of claim 30, wherein the cardiovascular parameters and variables include uncalibrated beat-by-beat end-diastolic volume.

41. The system of claim 40, wherein the computer executable instructions, when executed by the processor, cause the processor to compute calibrated beat-by-beat end-diastolic volume from the uncalibrated beat-by-beat end-diastolic volume using a second set of calibration parameters.

42. The system of claim 40, wherein the second set of calibration parameters is computed using an optimization criterion.

43. The system of claim 40, wherein the second set of calibration parameters is computed for each of the beats.

44. The system of claim 40, wherein the second set of calibration parameters include ventricular dead volume.

45. The system of claim 40, wherein the second set of calibration parameters include intra-thoracic pressure.

46. The system of claim 30, wherein the computer executable instructions, when executed by the processor, cause the processor to compute beat-by-beat cardiac contractility.

47. The system of claim 30, wherein the blood pressure measuring device is located at a central artery of the cardiovascular system.

48. The system of claim 47, wherein the central artery is the aorta.

49. The system of claim 30, wherein the blood pressure measuring device is located at a peripheral artery of the cardiovascular system.

50. The system of claim 30, wherein the blood pressure measuring device is located at a pulmonary artery of the cardiovascular system.

51. The system of claim 30, wherein the blood pressure measuring device is a noninvasive blood pressure device.

52. The system of claim 51, wherein the noninvasive blood pressure device is a photoplethysmographic blood pressure device.

53. The system of claim 51, wherein the noninvasive blood pressure device is a tonometric blood pressure device.

54. The system of claim 30, wherein processing the one or more cycles of arterial blood pressure includes obtaining a diastolic blood pressure; a peak-systolic blood pressure; and an end-systolic blood pressure for each cycle.

55. The system of claim 54, wherein the end-systolic blood pressure is estimated using an estimate of the duration of ventricular ejection.

56. The system of claim 55, wherein the estimate of the duration of ventricular ejection is obtained using phonocardiographic measurements.

57. The system of claim 30, wherein processing the one or more cycles of arterial blood pressure includes obtaining an onset time for each cycle.

58. The system of claim 30, wherein processing the one or more cycles of arterial blood pressure includes obtaining a beat duration for each cycle.

\* \* \* \* \*

UNITED STATES PATENT AND TRADEMARK OFFICE
CERTIFICATE OF CORRECTION

PATENT NO. : 8,235,910 B2  
APPLICATION NO. : 12/121878  
DATED : August 7, 2012  
INVENTOR(S) : Parlikar et al.

Page 1 of 1

It is certified that error appears in the above-identified patent and that said Letters Patent is hereby corrected as shown below:

In the Claims:

At column 23, claim number 18, line number 31, please delete "is" after "represents arterial blood pressure";

At column 23, claim number 20, line number 36, please delete "is" after "represents arterial blood pressure";

At column 23, claim number 21, line number 39, please delete "is" after "represents arterial blood pressure";

At column 23, claim number 22, line number 42, please delete "is" after "represents arterial blood pressure";

At column 23, claim number 23, line number 45, please delete "is" after "represents arterial blood pressure".

Signed and Sealed this  
Twentieth Day of November, 2012

David J. Kappos  
*Director of the United States Patent and Trademark Office*